United States Patent
T et al.

(10) Patent No.: US 10,957,451 B2
(45) Date of Patent: Mar. 23, 2021

(54) PATIENT HEALTHCARE INTERACTION DEVICE AND METHODS FOR IMPLEMENTING THE SAME

(71) Applicant: GENERAL ELECTRIC COMPANY, Schenectady, NY (US)

(72) Inventors: Satyanarayana T, Bangalore (IN); Abraham Gogulamudi, Bangalore (IN)

(73) Assignee: GENERAL ELECTRIC COMPANY, Schenectady, NY (US)

(*) Notice: Subject to any disclaimer, the term of this patent is extended or adjusted under 35 U.S.C. 154(b) by 393 days.

(21) Appl. No.: 15/910,686

(22) Filed: Mar. 2, 2018

(65) Prior Publication Data
US 2019/0198169 A1 Jun. 27, 2019

(30) Foreign Application Priority Data
Dec. 27, 2017 (IN) .............................. 201741046763

(51) Int. Cl.
| | |
|---|---|
| *G16H 50/20* | (2018.01) |
| *G16H 50/70* | (2018.01) |
| *G16H 40/20* | (2018.01) |
| *G16H 50/50* | (2018.01) |
| *G16H 10/60* | (2018.01) |

(Continued)

(52) U.S. Cl.
CPC .......... *G16H 50/20* (2018.01); *G06F 16/951* (2019.01); *G06N 20/00* (2019.01); *G16H 10/60* (2018.01); *G16H 40/20* (2018.01); *G16H 50/50* (2018.01); *G16H 50/70* (2018.01)

(58) Field of Classification Search
CPC ...................................................... G16H 40/20
See application file for complete search history.

(56) References Cited

U.S. PATENT DOCUMENTS

| | | | |
|---|---|---|---|
| 2009/0099862 A1 | 4/2009 | Fireman et al. | |
| 2010/0198755 A1* | 8/2010 | Soll ........................ | G16H 10/60 |
| | | | 706/11 |

(Continued)

FOREIGN PATENT DOCUMENTS

| | | | | |
|---|---|---|---|---|
| WO | WO-2007059477 A2 * | 5/2007 | ............. | G06T 19/00 |

*Primary Examiner* — Michael Tomaszewski
*Assistant Examiner* — Jay M. Patel
(74) *Attorney, Agent, or Firm* — Hanley, Flight & Zimmerman, LLC

(57) ABSTRACT

Methods, apparatus, and systems are disclosed to improve selection of medical treatment. An example apparatus includes a user interface to receive health information for a patient and a data analyzer to access historical patient information stored in a database, and determine a condition based on comparing historical patient information stored in a database to the health information for the patient. The example apparatus includes a machine learning engine to recommend a treatment plan, including: a data analytic algorithm server to determine success rates of the treatment plan for the condition; and a model generator to generate a patient model, wherein the patient model predicts effects of the treatment plan. The example apparatus includes a communications interface to facilitate scheduling an appointment with a clinician. The example apparatus includes the user interface to receive health tracking information from the patient indicative of the treatment plan effectiveness and store the health tracking information.

21 Claims, 29 Drawing Sheets

(51) Int. Cl.
    *G06N 20/00*     (2019.01)
    *G06F 16/951*     (2019.01)

(56) References Cited

U.S. PATENT DOCUMENTS

| | | | |
|---|---|---|---|
| 2010/0235295 A1* | 9/2010 | Zides | G06Q 30/0282 |
| | | | 705/347 |
| 2011/0077958 A1* | 3/2011 | Breitenstein | G06F 3/0484 |
| | | | 705/2 |
| 2011/0161096 A1 | 6/2011 | Buehler et al. | |
| 2015/0161461 A1* | 6/2015 | McNulty | G06K 9/00114 |
| | | | 382/116 |
| 2015/0338926 A1* | 11/2015 | Park | G06F 3/014 |
| | | | 345/156 |
| 2016/0342753 A1* | 11/2016 | Feazell | G16H 10/60 |
| 2017/0011210 A1* | 1/2017 | Cheong | G06F 21/32 |
| 2018/0158539 A1* | 6/2018 | Gupta | G16H 15/00 |
| 2018/0211726 A1* | 7/2018 | Courtemanche | G16H 40/67 |

* cited by examiner

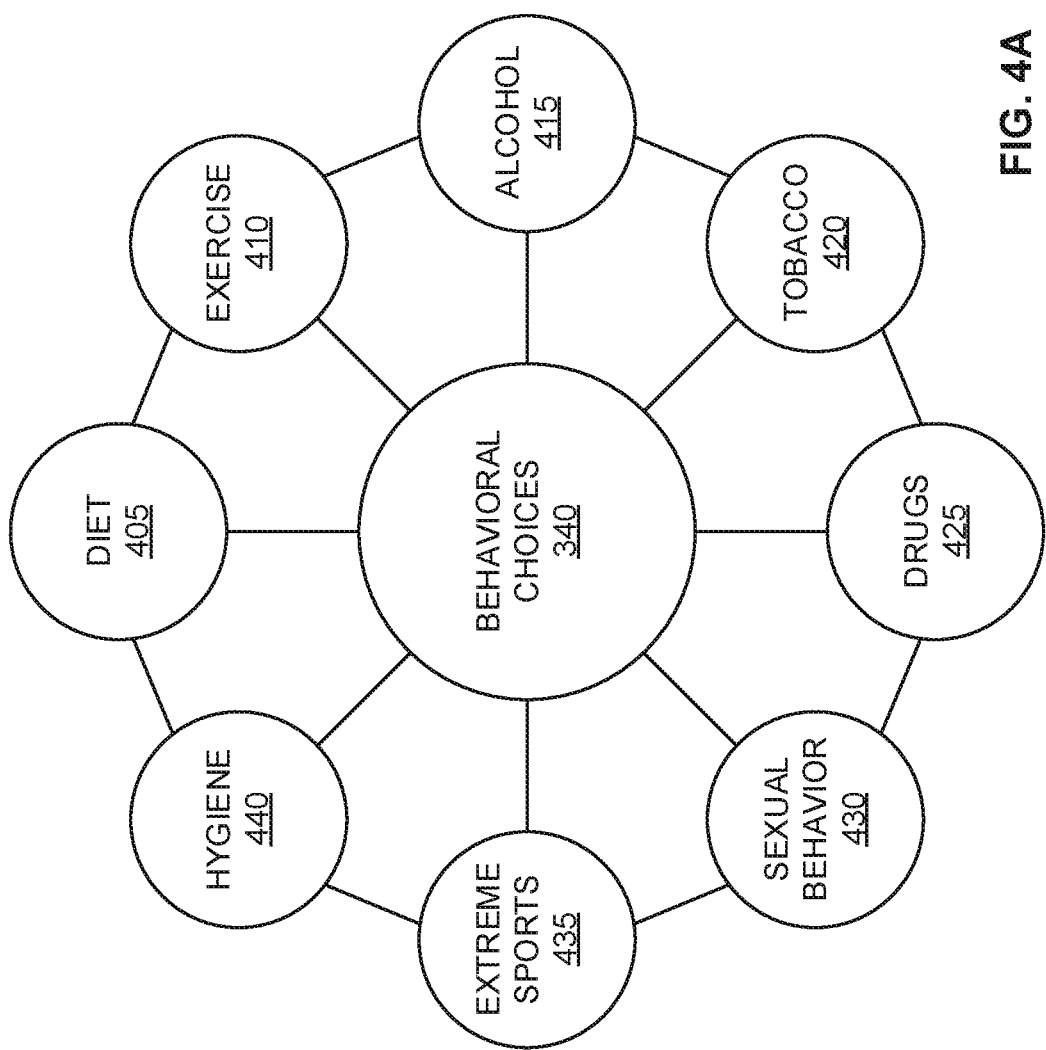

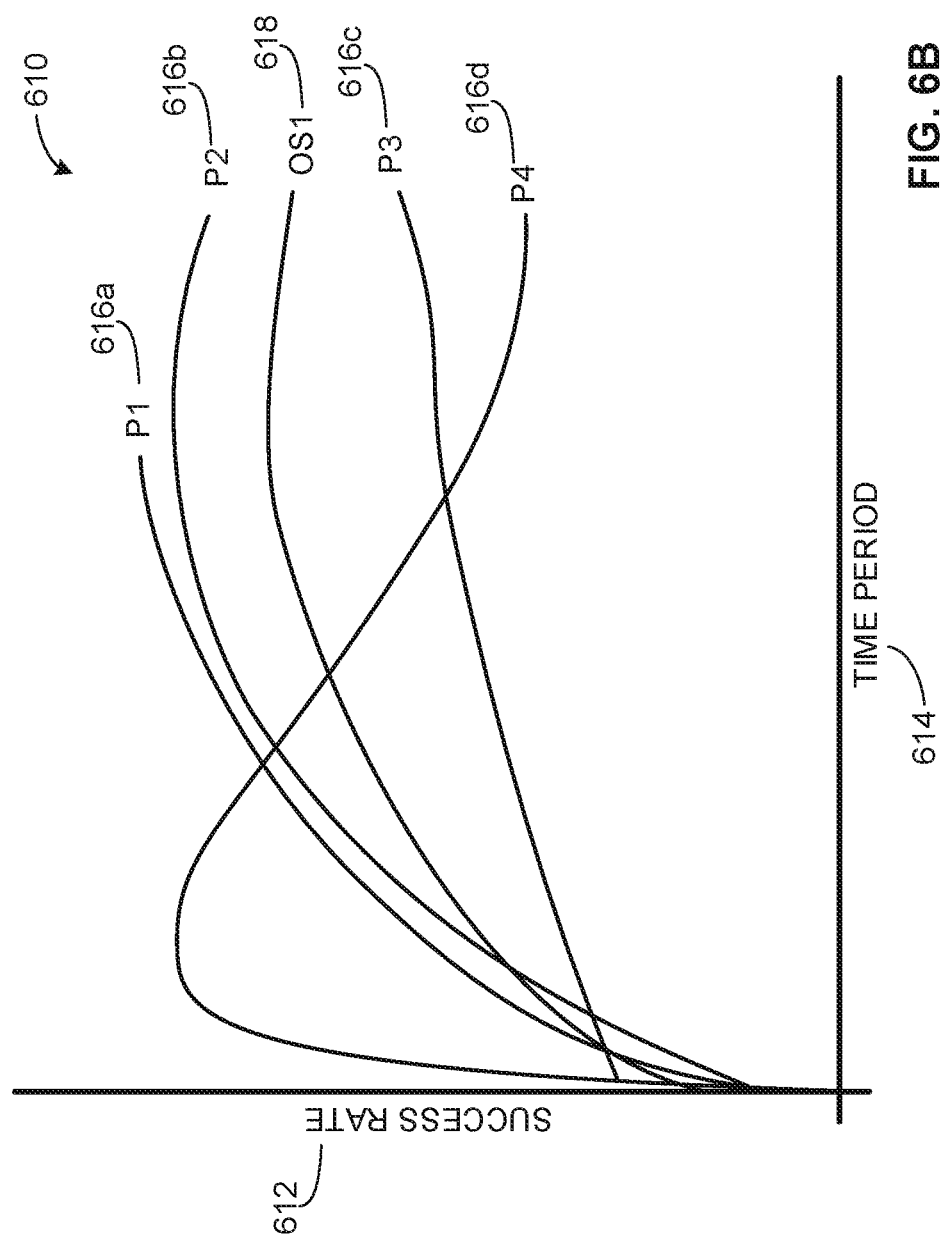

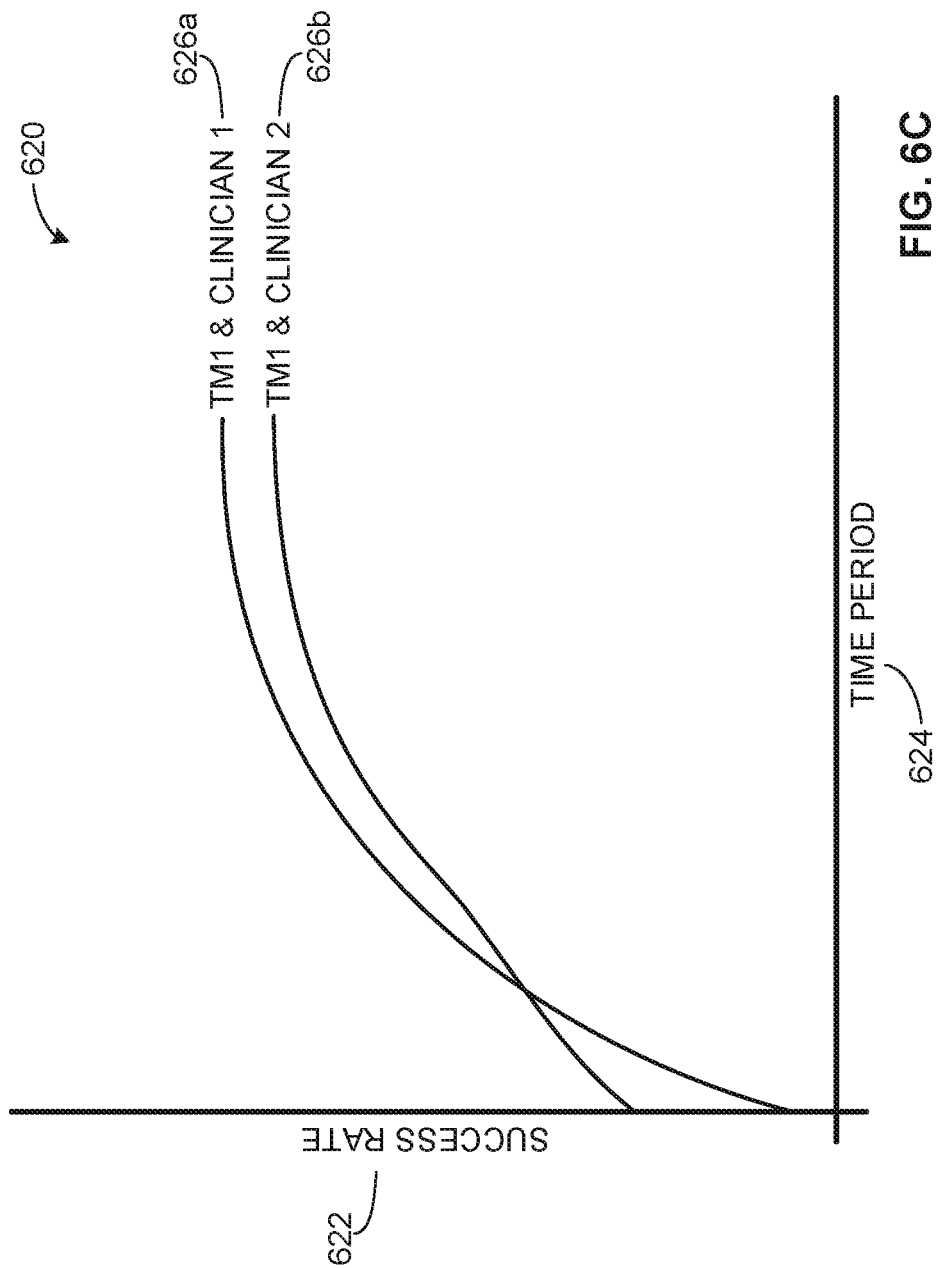

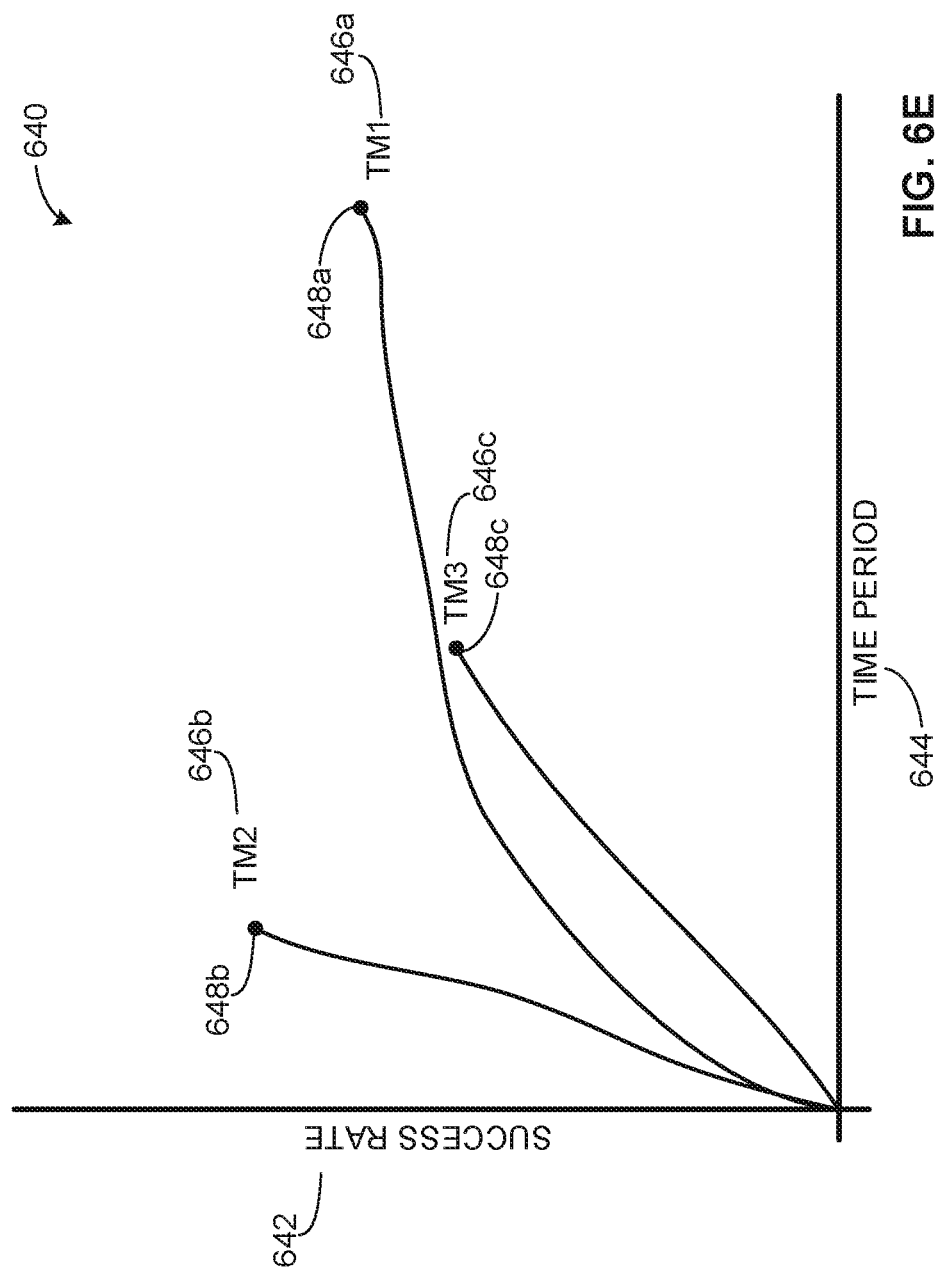

ions of FIGS. 12, 13, 14, 15A, 15B, 15C, 15D, 16,
PATIENT HEALTHCARE INTERACTION DEVICE AND METHODS FOR IMPLEMENTING THE SAME

RELATED APPLICATION

This patent claims the benefit of, and priority from, Indian Patent Application No. 201741046763, entitled "PATIENT HEALTHCARE INTERACTION DEVICE AND METHODS FOR IMPLEMENTING THE SAME," which was filed on Dec. 27, 2017. Indian Patent Application No. 201741046763 is hereby incorporated herein by reference in its entirety.

FIELD OF THE DISCLOSURE

This disclosure relates generally to a healthcare interaction device, and, more particularly, to methods and apparatus to a patient healthcare interaction device and methods for implementing the same.

BACKGROUND

Patients, after being diagnosed with a condition, are prescribed a treatment by a clinician. In some examples, treatment requires administration by medical professionals over several hospital visits. For example, some conditions require medical treatment to extend over several months. Often, the choice of treatment is made by the clinician based on their experience.

BRIEF DESCRIPTION OF THE DRAWINGS

FIGS. 4A and 4B illustrate an example model of behavioral choices and environmental or social determinants such as provided to/forming part of the digital twin in the example of FIG. 3.

FIGS. 6A, 6B, 6C, 6D, 6E, and 6F are example graphs indicating example condition treatment success rates and analytical data.

Figure 1:
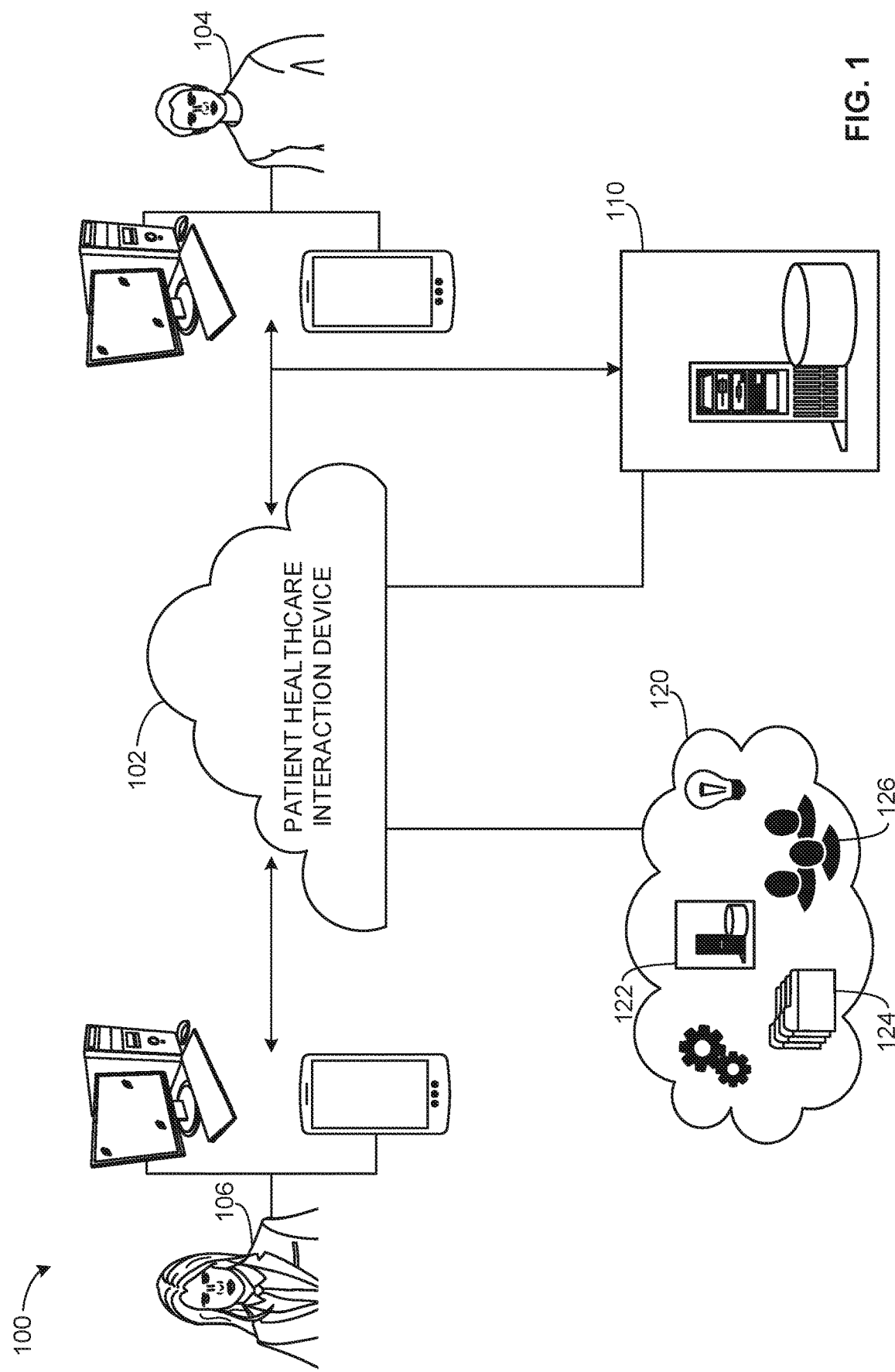
FIG. 1 illustrates an example system in which the examples disclosed herein can be implemented.

The figures are not to scale.

BRIEF SUMMARY

Methods, apparatus, systems, and articles of manufacture are disclosed for improved selection of condition treatment plans.

Certain examples provide an apparatus to select medical treatment including a user interface to receive health information for a patient, the health information including symptoms of a condition. The example system additionally includes a data analyzer to access historical patient information stored in a past patient database, and determine a condition based on comparing historical patient information stored in a past patient database to the health information for the patient. The example apparatus also includes a machine learning engine to recommend at least one treatment plan, to be presented by the user interface, including: a data analytic algorithm server to determine success rates of the at least one treatment plan for the condition, the success rates based on the health information for the patient and historical health information; and a model generator to generate a patient model, wherein the patient model predicts effects of the at least one treatment plan and symptoms of the condition for a duration of the treatment plan based on the success rates. The example apparatus additionally includes a communications interface to facilitate scheduling an appointment with a clinician, after the patient selects the treatment plan via the user interface. The example apparatus additionally includes the user interface to receive health tracking information from the patient indicative of a treatment plan effectiveness and store the health tracking information in a patient database.

Certain examples provide a computer implemented method to select medical treatment including receiving, via a user interface, health information for a patient, the health information including symptoms of a condition. The example computer implemented method also includes accessing, via a data analyzer, historical patient information stored in a past patient database. The example computer implemented method additionally includes determining, via a data analyzer, a condition based on comparing historical patient information stored in a past patient database to the health information for the patient. The example computer implemented method also includes recommending at least one treatment plan, to be presented by the user interface, by: determining success rates of the at least one treatment plan for the condition, via a data analytic algorithm server, the success rates based on the health information for the patient and historical health information; and generating a patient model, via a model generator, wherein the patient model predicts effects of the at least one treatment plan and symptoms of the condition for a duration of the treatment plan based on the success rates. The example computer implemented method additionally includes scheduling an appointment with a clinician, via a communication interface, after the patient selects the treatment plan via the user interface. The example computer implemented method also includes receiving, via the user interface, health tracking information from the patient indicative of a treatment plan effectiveness and store the health tracking information in a patient database.

Certain examples provide a non-transitory computer readable storage medium comprising computer readable instructions to select medical treatment, that, when executed, cause a processor to at least receive health information for a patient, the health information including symptoms of a condition. The example instructions that, when executed, cause the at least one processor to access historical patient information stored in a past patient database. The example instructions that, when executed, cause the at least one processor to determine a condition based on comparing historical patient information stored in a past patient database to the health information for the patient. The example instructions that, when executed, cause the at least one processor to recommend at least one treatment plan, to be presented by a user interface, based on the instructions further causing the processor to: determine success rates of the at least one treatment plan for the condition, the success rates based on the health information for the patient and historical health information; and generate a patient model, wherein the patient model predicts effects of the at least one treatment plan and symptoms of the condition for a duration of the treatment plan based on the success rates. The example instructions that, when executed, cause the at least one processor to facilitate scheduling an appointment with a clinician, after the patient selects the treatment plan via the user interface. The example instructions that, when executed, cause the at least one processor to and receive health tracking information from the patient indicative of a treatment plan effectiveness and store the health tracking information in a patient database.

DETAILED DESCRIPTION

People are regularly concerned with their health and will utilize technology to access information concerning conditions, doctors, and treatments. However, this information can often be difficult to access or inaccurate. In some examples, the self-diagnosis is improper, while in other examples, the treatment is ineffective or even detrimental to the health of a person. Additionally, people can be referred to a clinician (e.g., a doctor, registered nurse, physician's assistant, nurse, pharmacist, etc.) with a specialty incongruous with the condition currently affecting the patient.

In some examples, patients are often diagnosed with a condition by a clinician. Some conditions may require extensive treatment plans. The clinician of the patient may recommend a treatment plan for the condition, but the treatment can, for example, not be the best treatment plan available for the condition or be overly burdensome for the patient. The clinician can be unfamiliar with the condition or inexperienced with newer treatment plans that would be better for the patient. In such examples, the patient is not receiving the best health care for their diagnosed condition.

Treatment for some conditions can take months and numerous hospital visits. Other treatments may require administration of medicines that cause adverse side effects for the duration of the administration. As a result, some treatment plans are not completed because the treatment plan is too difficult for the patient to complete, and the health of the patient is adversely affected by temporary side effects.

For example, if a patient is diagnosed with Retinal Vasculitis, a clinician may prescribe a steroid to treat the disease. The patient, attempting the treatment, finds the condition has deteriorated. The patient then can seek a second clinician that prescribes a different steroid to be administered with laser treatment. The patient may find the treatment partially successful, but upon the advice of a friend, seeks out a clinician that specializes in homeopathy treatments. The patient finds that after the homeopathy treatment, the disease is fully treated. In typical medical centers, the success rate of the three treatment plans is not recorded, and each clinician would continue to administer their treatment plans. Additionally, future patients may be administered the treatment plans with low success rates.

In accordance with the present disclosure, the patient and clinician are provided information regarding success rates of treatment plans based on the patient information and the diagnosed condition. In some examples, a success rate of clinicians treating a condition is also provided to the patient. Additionally, patients can discuss the treatment plan with past patients to best understand what to expect with a given treatment plan. As a result, helping the patient select the clinician and treatment plan and informing the patient of the difficulties associated with the treatment plan helps improve the overall success rate of patients being treated for conditions.

For example, after being diagnosed with a condition, a patient's information is input into the patient healthcare interaction device. The information can include age, race, sex, medical history, and condition diagnosis. The patient healthcare interaction device processes the patient information via the patient healthcare interaction device model and provides the patient with a success rate. In some examples, the success rate is displayed having three axes (e.g., three-dimensional (3-D)). In other examples, the patient healthcare interaction device can generate a digital "twin" of the patient to predict the outcome of several possible treatment plans including success rates and complications based on historical data of similar patients. Additionally or alternatively, the success rate and/or the digital twin can, in some examples, be displayed in a virtual or augmented reality environment.

The digital twin is a digital representation (e.g., digital model, digital "shadow," etc.) of the patient in the form of a digital informational construct about a physical system.

That is, digital information can be implemented as a "twin" of a physical device/system/person and information associated with and/or embedded within the physical device/system. The digital twin is linked with the physical system through the lifecycle of the physical system. In certain examples, the digital twin includes a physical object in real space, a digital twin of that physical object that exists in a virtual space, and information linking the physical object with its digital twin. The digital twin exists in a virtual space corresponding to a real space and includes a link for data flow from real space to virtual space as well as a link for information flow from virtual space to real space and virtual sub-spaces. For example, the digital twin can predict the real effects of stimuli on the physical object in real space.

In some examples, the patient is given the option of contacting other patients currently or previously undergoing similarly recommended treatments. By being able to anonymously contact past patients, the instant patient can better understand the side effects, success, complications, etc., from undergoing treatment. Understanding the treatment helps the patient select the treatment that best fits their life or better prepare for the treatment plan. Additionally or alternatively, the past patients can commend the benefits of following through with a treatment plan despite side effects or complications, thus encouraging the instant patient to undergo a difficult treatment plan such as chemotherapy, extensive surgery, etc.

During and after the treatment of the condition, patient treatment data is input into the system. During the treatment, various health tracker systems can be used to input patient treatment data such as Apple Healthkit™, Google Fit™, Microsoft HealthVault™, etc. The treatment data provided by the activity and health tracking systems is used to provide the patient healthcare interaction device with daily metrics of patient health before, during, and after treatment. Additionally, more detailed patient information can be gathered during medical center visits including blood tests, urinalysis, neurological exams, etc. and input into the patient health treatment system database. In some examples, the data also includes number of medical center visits and duration of the visits, satisfaction with the clinician or the treatment, and the overall success of the treatment. By providing this information to the digital twin model, the patient healthcare interaction device can provide more accurate and up-to-date treatment information.

Use of a digital twin model based on regularly updated patient information provides patients and/or clinicians with accurate information regarding success, side effects, and complications of a variety of treatment plans for a given condition diagnosis. By improving access to up-to-date information, the clinician is better equipped to prescribe treatment plans best fit for the patient, and the patient can be informed of the success rates of the treatment plan and be mindful of the possible side effects and complications. With this information, patients can receive better healthcare and endure difficulties of certain treatment plans in hope of the success of the treatment.

FIG. 1 illustrates an example environment 100 in which an example patient healthcare interaction device 102 disclosed herein can be implemented. In the illustrated example of FIG. 1, the environment 100 includes a patient 104 and a clinician 106. In other examples, the environment 100 includes more than one patient 104 and more than one clinician 106. Additionally, in the illustrated example of FIG. 1, both the clinician 106 and the patient 104 are interacting with the patient healthcare interaction device 102, however in other examples, the clinician 106 interacts with the patient healthcare interaction device 102 on behalf of the patient 104.

In some examples, the patient 104 interacts with the patient healthcare interaction device 102 to input health information 110 including condition symptoms. For example, in addition to condition symptoms, health information 110 can include sex, height, weight, tobacco usage, alcohol consumption, diet, exercise, allergies, medical history, cholesterol, resting heart rate, etc. In some examples, based on the health information 110, the patient healthcare interaction device 102 suggests a possible condition diagnosis. In other examples, the clinician 106 reviews the health information to diagnose the patient 104.

After the patient healthcare interaction device 102 provides a condition diagnosis that is confirmed by the clinician 106 or the clinician 106 inputs into the patient healthcare interaction device 102 the condition diagnosis, the patient healthcare interaction device 102 generates analytical data and a model to determine treatment plan success rates for the condition. In accordance with the present disclosure, the model is a digital twin of the patient 104 based on the health information 110 provided. In other examples, the model may be a convolutional neural network (CNN) or other artificial intelligence system.

The example digital twin of the patient 104 generated by the patient healthcare interaction device 102 is based on the analytical data and health information 110 provided by the patient 104 and historical data 120 on treatment of the diagnosed condition. In some examples, historical data 120 can include past patient health information 122, treatment success rates of previous patients 124, and testimonials of previous patients 126. For example, the digital twin can be generated to mimic the height, weight, and other health information 110 of the patient 104, but determine treatment response from the patient 104 based primarily on past patients with similar health information and based to a lesser extent past patients with different health information. For example, smoking cigarettes can affect short term inhaled corticosteroid usage. As a result, if the patient 104 smokes cigarettes, their digital twin should indicate a reduced response to inhaled corticosteroid usage compared to non-smokers, perhaps even if inhaled corticosteroids are the best treatment plan for nonsmokers. In other examples, men and women metabolize medications differently, and their treatment plans can vary based on prescribed dosages. As a result, the patient healthcare interaction device 102 compares past patient health information 122 to the health information 110 of the patient 104 to generate analytical data and generate a digital twin that can respond to a digital treatment as the patient 104 will respond to the selected treatment.

In some examples, the patient 104 updates their health information via a health tracker such as Apple Healthkit™, Google Fit™, Microsoft HealthVault™, etc. For example, these health trackers can provide health and activity information for the patient 104 and accordingly update the health information 110 during treatment. As a result, the clinician 106 can have access to the hours spent resting or active, daily weight gain and weight loss during the treatment, resting heart rate, etc. In some examples, this information can be used to track the treatment plan effectiveness and/or any side effects. For example, the health tracking information can indicate if resting improves the effectiveness of a treatment, or if a treatment is likely to result in weight loss. This information can be very important in selecting a treatment plan for the patient 104.

Figure 2:
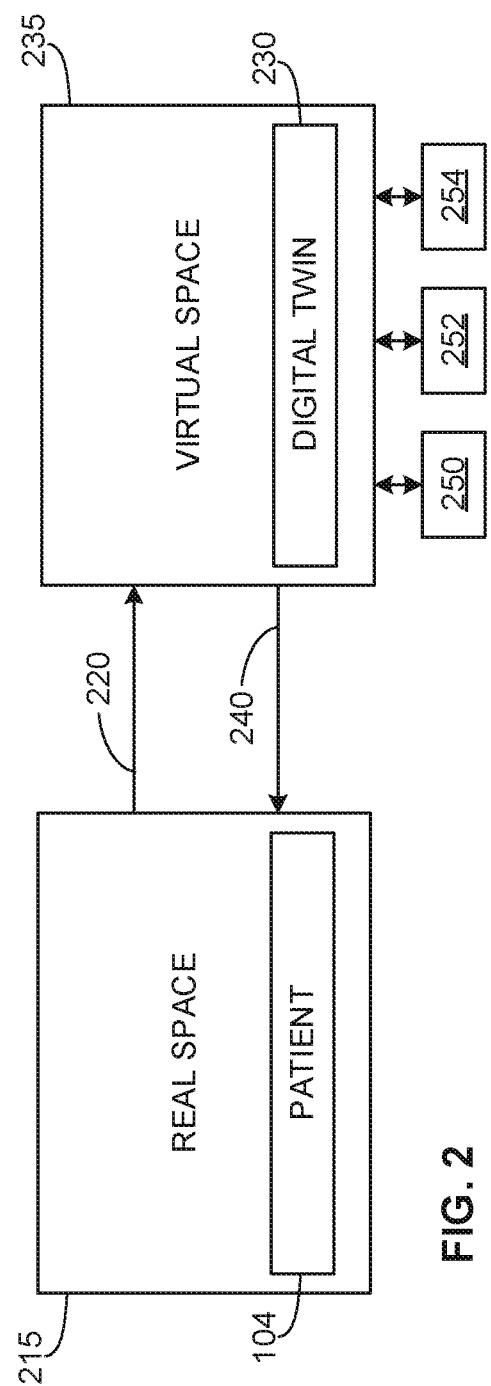
FIG. 2 illustrates an example implementation of a patient digital twin.

FIG. 2 illustrates a patient 104 in a real space 215 providing data 220 to a digital twin 230 in a virtual space 235. The digital twin 230 and/or its virtual space 235 provide information 240 back to the real space 215. The digital twin 230 and/or virtual space 235 can also provide information to one or more virtual sub-spaces 250, 252, 254. As shown in the example of FIG. 2, the virtual space 235 can include and/or be associated with one or more virtual sub-spaces 250, 252, 254, which can be used to model one or more parts of the digital twin 230 and/or digital "sub-twins" modeling subsystems/subparts of the overall digital twin 230.

Sensors connected to the physical object (e.g., the patient 104) can collect data and relay the collected data 220 to the digital twin 230 (e.g., via self-reporting, using a clinical or other health information system such as a picture archiving and communication system (PACS), radiology information system (RIS), electronic medical record system (EMR), laboratory information system (LIS), cardiovascular information system (CVIS), hospital information system (HIS), and/or combination thereof, etc.). Interaction between the digital twin 230 and the patient 104 can help improve diagnosis, treatment, health maintenance, etc., for the patient 104, for example. An accurate digital description 230 of the patient 104 benefiting from a real-time or substantially real-time (e.g., accounting for data transmission, processing, and/or storage delay) allows the system to predict "failures" in the form of condition, body function, and/or other malady, condition, etc.

In certain examples, obtained images overlaid with sensor data, lab results, etc., can be used in augmented reality (AR) applications when a healthcare practitioner is examining, treating, and/or otherwise caring for the patient 104. Using AR, the digital twin 230 follows the patient's response to the interaction with the healthcare practitioner, for example.

Thus, rather than a generic model, the digital twin 230 is a collection of actual physics-based, anatomically-based, and/or biologically-based models reflecting the patient 104 and his or her associated norms, conditions, etc. In certain examples, three-dimensional (3D), predictive modeling of the patient 104 creates the digital twin 230 for the patient 104. The digital twin 230 can be used to view a status of the patient 104 based on input data 220 dynamically provided from a source (e.g., from the patient 104, practitioner, health information system, sensor, etc.).

In certain examples, the digital twin 230 of the patient 104 can be used for monitoring, diagnostics, and prognostics for the patient 104. Using sensor data in combination with historical information, current and/or potential future conditions of the patient 104 can be identified, predicted, monitored, etc., using the digital twin 230. Causation, escalation, improvement, etc., can be monitored via the digital twin 230. Using the digital twin 230, the patient's 210 physical behaviors can be simulated and visualized for diagnosis, treatment, monitoring, maintenance, etc.

In contrast to computers, humans do not process information in a sequential, step-by-step process. Instead, people try to conceptualize a problem and understand its context. While a person can review data in reports, tables, etc., the person is most effective when visually reviewing a problem and trying to find its solution. Typically, however, when a person visually processes information, records the information in alphanumeric form, and then tries to re-conceptualize the information visually, information is lost and the problem-solving process is made much less efficient over time.

Using the digital twin 230, however, allows a person and/or system to view and evaluate a visualization of a situation (e.g., a patient 104 and associated patient problem, etc.) without translating to data and back. With the digital twin 230 in common perspective with the actual patient 104, physical and virtual information can be viewed together, dynamically and in real time (or substantially real-time accounting for data processing, transmission, and/or storage delay). Rather than reading a report, a healthcare practitioner can view and simulate with the digital twin 230 to evaluate a condition, progression, possible treatment, etc., for the patient 104. In certain examples, features, conditions, trends, indicators, traits, etc., can be tagged and/or otherwise labeled in the digital twin 230 to allow the practitioner to quickly and easily view designated parameters, values, trends, alerts, etc.

The digital twin 230 can also be used for comparison (e.g., to the patient 104, to a "normal", standard, or reference patient, set of clinical criteria/symptoms, etc.). In certain examples, the digital twin 230 of the patient 104 can be used to measure and visualize an ideal or "gold standard" value state for that patient, a margin for error or standard deviation around that value (e.g., positive and/or negative deviation from the gold standard value, etc.), an actual value, a trend of actual values, etc. A difference between the actual value or trend of actual values and the gold standard (e.g., that falls outside the acceptable deviation) can be visualized as an alphanumeric value, a color indication, a pattern, etc.

Further, the digital twin 230 of the patient 104 can facilitate collaboration among friends, family, care providers, etc., for the patient 104. Using the digital twin 230, conceptualization of the patient 104 and his/her health can be shared (e.g., according to a care plan, etc.) among multiple people including care providers, family, friends, etc. People do not need to be in the same location as the patient 104, with each other, etc., and can still view, interact with, and draw conclusions from the same digital twin 230, for example.

Thus, the digital twin 230 can be defined as a set of virtual information constructs that describes (e.g., fully describes) the patient 104 from a micro level (e.g., heart, lungs, foot, anterior cruciate ligament (ACL), stroke history, etc.) to a macro level (e.g., whole anatomy, holistic view, skeletal system, nervous system, vascular system, etc.). In certain examples, the digital twin 230 can be a reference digital twin (e.g., a digital twin prototype, etc.) and/or a digital twin instance. The reference digital twin represents a prototypical or "gold standard" model of the patient 104 or of a particular type/category of patient 104, while one or more reference digital twins represent particular patients 104. Thus, the digital twin 230 of a child patient 104 may be implemented as a child reference digital twin organized according to certain standard or "typical" child characteristics, with a particular digital twin instance representing the particular child patient 104. In certain examples, multiple digital twin instances can be aggregated into a digital twin aggregate (e.g., to represent an accumulation or combination of multiple child patients sharing a common reference digital twin, etc.). The digital twin aggregate can be used to identify differences, similarities, trends, etc., between children represented by the child digital twin instances, for example.

In certain examples, the virtual space 235 in which the digital twin 230 (and/or multiple digital twin instances, etc.) operates is referred to as a digital twin environment. The virtual space 235 provides an integrated, multi-domain physics- and/or biologics-based application space in which to operate the digital twin 230. The digital twin 230 can be analyzed in the virtual space 235 to predict future behavior, condition, progression, etc., of the patient 104, for example. The digital twin 230 can also be interrogated or queried in the virtual space 235 to retrieve and/or analyze current information 240, past history, predict real effects to stimuli, etc.

In certain examples, the virtual space 235 can be divided into multiple virtual spaces 250, 252, 254. Each virtual space 250, 252, 254 can model a different digital twin instance and/or component of the digital twin 230 and/or each virtual space 250, 252, 254 can be used to perform a different analysis, simulation, etc., of the same digital twin 230. Using the multiple virtual spaces 250, 252, 254, the digital twin 230 can be tested inexpensively and efficiently in a plurality of ways while preserving patient 104 safety. A healthcare provider can then understand how the patient 104 may react to a variety of treatments in a variety of scenarios, for example.

Figure 3:
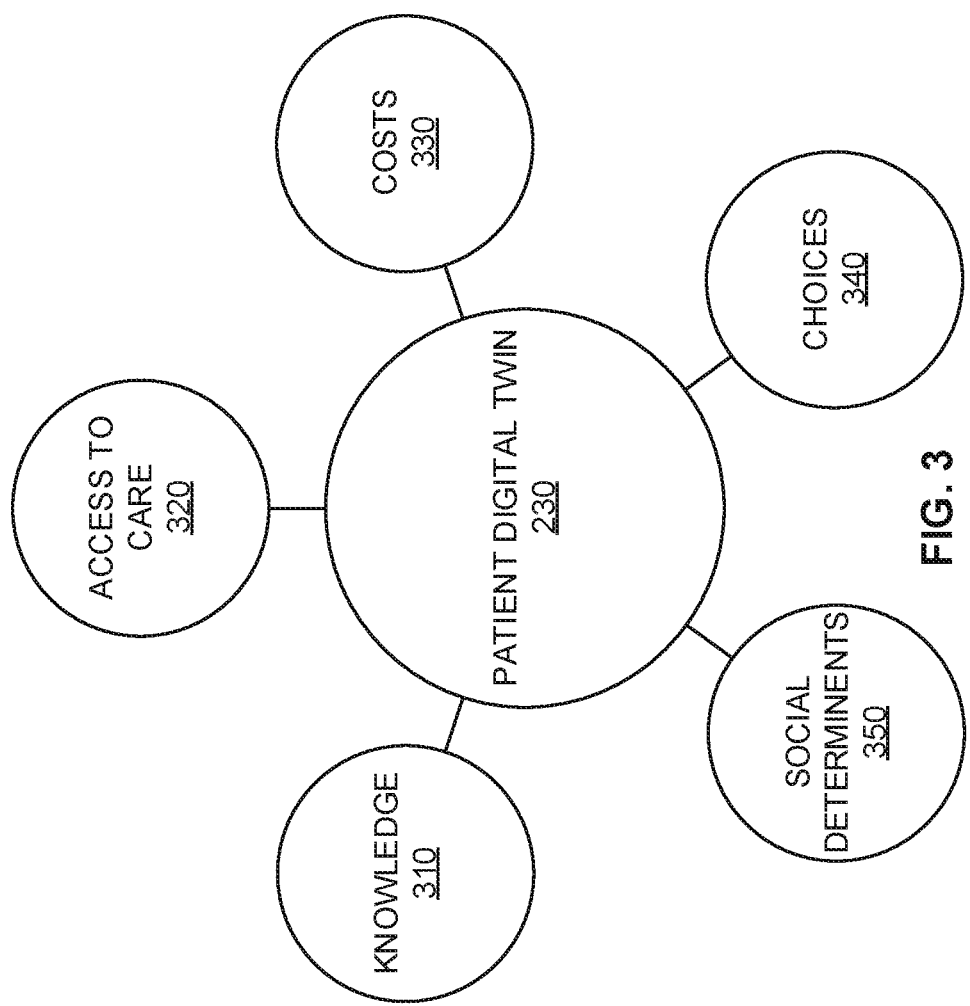
FIG. 3 illustrates an example relationship between a patient digital twin and advanced coordinated technologies to achieve patient outcomes.

FIG. 3 illustrates an example relationship between a patient digital twin 230 and advanced coordinated technologies to achieve patient outcomes. The patient digital twin 230 can be used to apply patient-related heterogenous data with artificial intelligence (e.g., machine learning, deep learning, etc.) and digitized medical knowledge to enable health outcomes. As shown in the example of FIG. 3, the patient digital twin 230 can be used to drive applied knowledge 310, access to care 320, costs 330, personal choices 340, social determinants/environment 350, etc. For example, the drive applied knowledge 310 can include information from sources including rules, guidelines, medical science, molecular science, medical journals, etc. Additionally, the example access to care 320 can include information regarding clinic access, hospital access, access to medical technology, etc. In some examples, information regarding the costs 330 is determined based on known costs of hospital or medical facilities, medications, usage of medical technologies, etc. The information for drive applied knowledge 310, access to care 320, and costs 330 are typically not provided by the patient 104. However, behavioral choices 340 and environment 350 include information specific to patient 104. FIGS. 4 and 5 provide further detail regard each of the behavioral choice 340 and environment 350 of the example patient digital twin 230 of FIG. 3.

FIG. 4A illustrates an example model of behavioral choices such as provided to/forming part of the digital twin in the example of FIG. 3. As shown in the example of FIG. 4A, information regarding behavioral choices 340 includes diet 405, exercise 410, alcohol 415, tobacco 420, drugs 425, sexual behavior 430, extreme sports 435, hygiene 440, etc. Behavioral information 405, 410, 415, 420, 425, 430, 435, 440 can be provided by the patient 104 of FIG. 1, the clinician 106 of FIG. 1, other healthcare practitioners, coaches, social workers, family, friends, etc. Additionally, behavioral information 405, 410, 415, 420, 425, 430, 435, 440 can be provided by medical devices, monitoring devices, biometric sensors, locational sensors, communication systems, collaboration systems, etc. For example, devices including Apple Healthkit™, Google Fit™, Microsoft HealthVault™ and similar health and activity trackers can sync activity and patient vitals with the digital twin 230. Behavioral choices 340 observed in and/or documented with respect to the patient 104 can be reflected in the patient's digital twin 230, and rules, consequences, and/or other outcomes of certain behaviors 405, 410, 415, 420, 425, 430, 435, 440 can be modeled via the digital twin 230, for example.

Figure 4B:
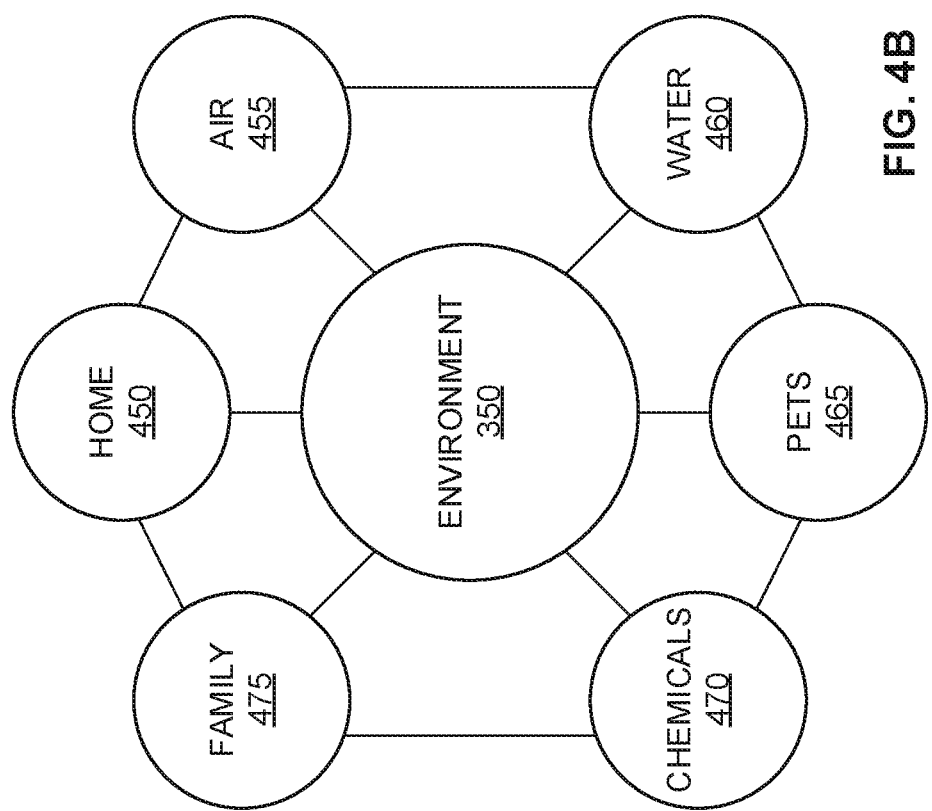
Figure 5:
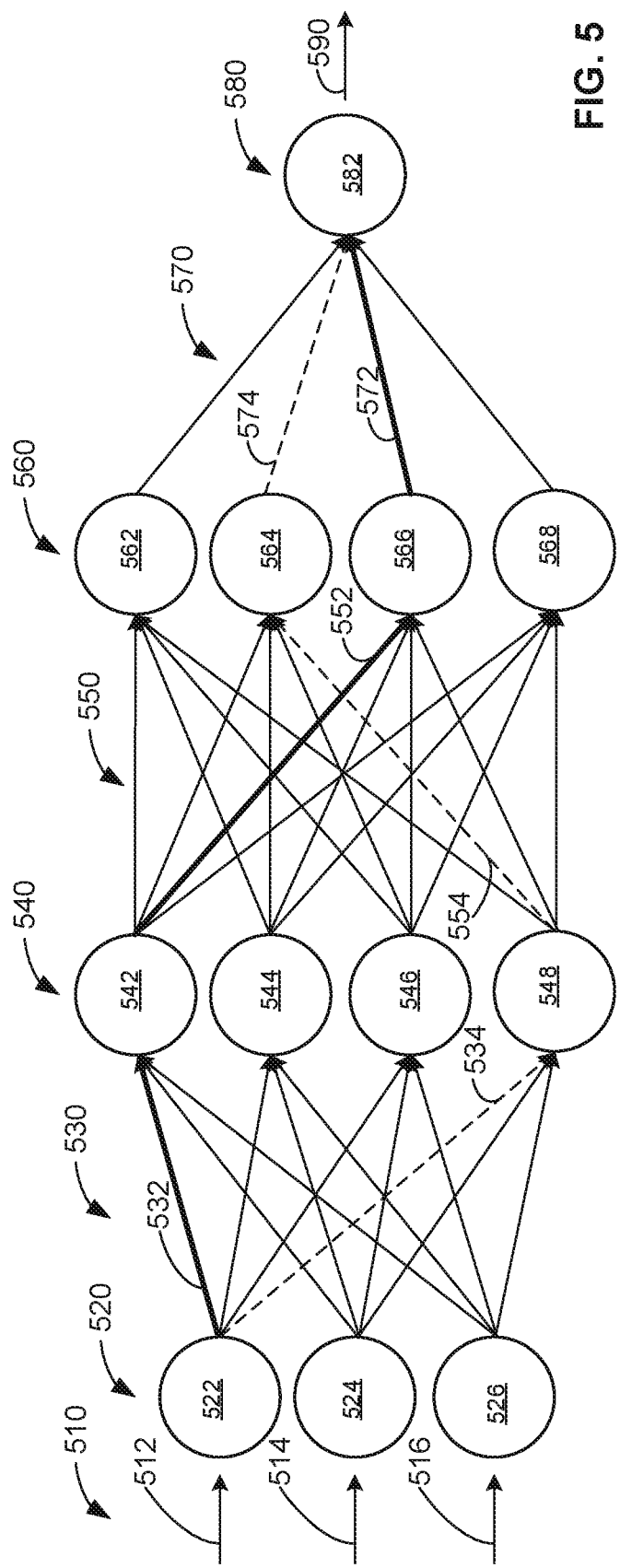
FIG. 5 is a representation of an example deep learning neural network that can be used to implement the patient digital twin.

FIG. 4B illustrates an example model of environmental factors or social determinants such as provided to/forming part of the digital twin in the example of FIG. 3. As shown in the example of FIG. 4B, information regarding environmental factors 350 can include home 450, air 455, water 460, pets 465, chemicals 470, family 475, etc. Thus, one or more social/environmental factors 350 can be modeled for the patient 104 via the patient's digital twin 230. In certain examples, community resources, medical devices, monitoring devices, biometric sensors, geographic data, locational sensors, communication systems, collaboration systems, etc., can be used to measure and/or otherwise capture social/environmental information 350 to be modeled via the patient digital twin 230, for example. Social/environmental factors 450, 455, 460, 465, 470, 475 can influence patient 104 behavior, health, recovery, adherence to protocol, etc., and such factors 450, 455, 460, 465, 470, 475 can be modeled by the digital twin 230, for example.

FIG. 5 is a representation of an example deep learning neural network that can be used to implement the patient digital twin. The example neural network 500 includes layers 520, 540, 560, and 580. The layers 520 and 540 are connected with neural connections 530. The layers 540 and 560 are connected with neural connections 550. The layers 560 and 580 are connected with neural connections 570. Data flows forward via inputs 512, 514, 516 from the input layer 520 to the output layer 580 and to an output 590.

The layer 520 is an input layer that, in the example of FIG. 5, includes a plurality of nodes 522, 524, 526. The layers 540 and 560 are hidden layers and include, the example of FIG. 5, nodes 542, 544, 546, 548, 562, 564, 566, 568. The neural network 500 may include more or less hidden layers 540 and 560 than shown. The layer 580 is an output layer and includes, in the example of FIG. 5, a node 582 with an output 590. Each input 512-516 corresponds to a node 522-526 of the input layer 520, and each node 522-526 of the input layer 520 has a connection 530 to each node 542-548 of the hidden layer 540. Each node 542-548 of the hidden layer 540 has a connection 550 to each node 562-568 of the hidden layer 560. Each node 562-568 of the hidden layer 560 has a connection 570 to the output layer 580. The output layer 580 has an output 590 to provide an output from the example neural network 500.

Of connections 530, 550, and 570 certain example connections 532, 552, 572 may be given added weight while other example connections 534, 554, 574 may be given less weight in the neural network 500. Input nodes 522-526 are activated through receipt of input data via inputs 512-516, for example. Nodes 542-548 and 562-568 of hidden layers 540 and 560 are activated through the forward flow of data through the network 500 via the connections 530 and 550, respectively. Node 582 of the output layer 580 is activated after data processed in hidden layers 540 and 560 is sent via connections 570. When the output node 582 of the output layer 580 is activated, the node 582 outputs an appropriate value based on processing accomplished in hidden layers 540 and 560 of the neural network 500.

Figure 6A:
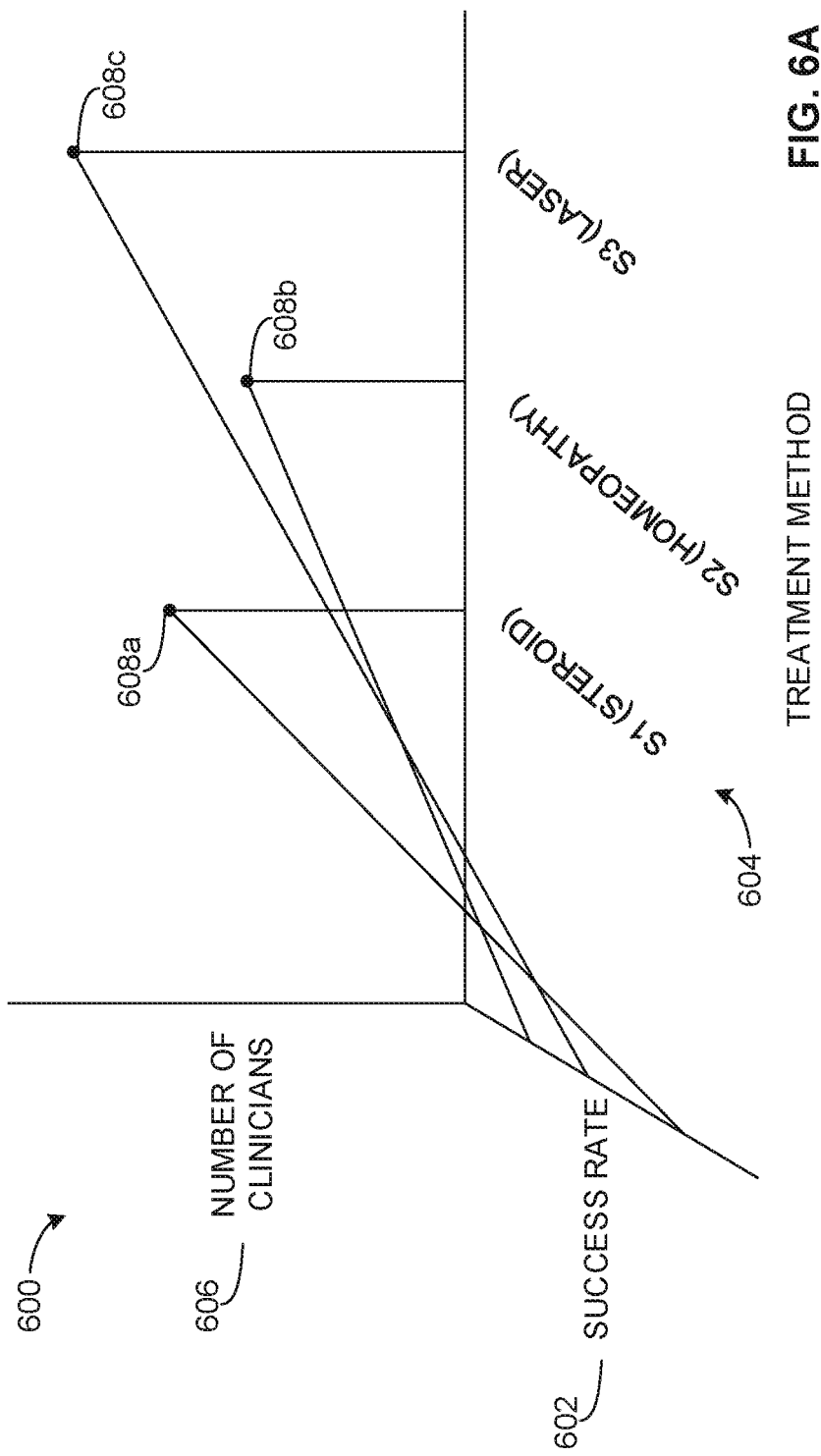

FIG. 6A is an example graph 600 indicating example condition treatment success rates 602 generated by the patient healthcare interaction device 102 of FIG. 1. In the illustrated example of FIG. 6A, the graph 600 has three treatments 604. In other examples, the graph 600 can include additional treatments 604 or combinations of treatments 604. Additionally, on a third axis 606, the example graph 600 indicates a number of clinicians prescribing any of the treatments 604. In other examples, the third axis 606 may indicate a number of patients prescribed with any of the treatments 604 for all clinicians for which data is available. Additionally or alternatively, for some conditions, the third axis 606 can indicate a number of patients prescribed with any of the treatments for a single clinician.

In accordance with the present disclosure, the success rate 602 is calculated based on, for example, a number of visits to a medical center for the same or a similar issue, duration of medical center visits, extent of side effects, duration of condition, outcome, etc. In other examples, the patient healthcare interaction device 102 of FIG. 1 can also generate a complications graph indicating a likelihood of complications for a given treatment.

As illustrated in the example of FIG. 6A, the success rate is calculated based on past patient information. For example, the success rate is calculated based on three factors: (1) overall experience of clinician treatment divided by the number of visits, (2) number of revisits for a similar or same condition, and (3) number of visits to a different medical center for a similar or same condition. In some examples, the three factors can be weighted with priority (e.g., a multiplicand). For example, an overall visit experience (OVE) for a single patient can be calculated as, OVE=20=(40 (first visit)+20 (second visit)+10 (third visit)+10 (fourth visit))/4. In other examples, the success rate can be calculated based on different factors and equations. The calculated success rate and/or OVE can be applied to the machine learning engine to improve recommendations for a second or subsequent patient.

For example, a first patient's experience can be captured, analyzed, and modeled/quantified so that a second patient can leverage the first patient's experience (and the first patient can benefit from past experience in a future visit, etc.). A success rate can be determined according to a plurality of quotients or factors representing feature priority including: x1 (overall experience of a doctor's treatment as indicated by patients of that doctor), x2 (a number of patient re-visits to same healthcare facility for the same/similar issue), x3 (patient visit to a different healthcare facility for the same/similar issue), etc. Thus, the success rate can be calculated as:

$$SuccessRate = x1/\text{number of visits} + x2 - x3 \quad \text{(Eq. 1)}.$$

Thus, an overall experience of a healthcare practitioner's treatment can be evaluated from patient outcomes and feedback for a plurality of patients over time.

As an example, the first patient's success rate can be calculated from the following feature set:

Doctor 1(only steroid):10($1^{st}$Visit)−50($2^{nd}$ Visit)+30 ($3^{rd}$ Visit)−30($4^{th}$Visit)=−40

Doctor 2(steroid+laser):−40($1^{st}$ Visit)+40($2^{nd}$ Visit)+ 40($3^{rd}$ Visit)+($4^{th}$Visit)+0($5^{th}$ visit)+0($6^{th}$ Visit) =40

Doctor 3(homeopathy):40($1^{st}$ Visit)+20($2^{nd}$ Visit)+10 ($3^{rd}$ Visit)+10($4^{th}$Visit)+0($5^{th}$ visit)=80

An analytical result such as the three-dimensional (3D) diagram of FIG. 6A can be presented to enable and/or otherwise facilitate determination of a healthcare practitioner for treatment. In certain examples, multiple clinicians can be selected to treat a patient's condition, and a selected clinician can combine treatment approaches from multiple prior clinicians. For example, per FIG. 6A, a doctor can choose to use homeopathy to reduce inflammation as well as laser to avoid current complications including due to use of steroid. Thus, while current medical practice and technology do not support such evaluation of success rate and combination of treatment techniques, certain examples provide technological improvements to enable such processing and combination, for example.

Thus, patient experience can be modeled (e.g., using a patient digital twin, artificial neural network, and/or other machine learning construct, etc.) to generate a success rate factor that enables patients to make better decisions at an earlier point in time to get better treatment. Multiple feature sets can be used to generate the success rate factor. A user interactable interface can display and facilitate interaction with the analyzed result. Use of a connectivity protocol (e.g., a secure Web-based interface, etc.) avoids security vulnerabilities and protects patient information while providing technology to facilitate conversation and exchange of information.

In certain examples, if a plurality of prior patients is available for discussion and/or other analysis, the available patients and their associated success rate can be processed to determine which prior patient(s) are best to connect to the current patient/provider. In certain examples, selection of a success rate factor from a plurality of success rate factors triggers display and interaction with a list of prior experiences meeting that success rate factor and/or range of success rate factors.

For example, if John, Mark, and Justin are available for collaboration, their respective success rates are compared. John has a success rate of Visit1*10+Visit2*−20+ Visit3*40+Visit4*60; Mark has a success rate of Visit1*10+ Visit2*−5+Visit3*10+Visit4*10; and Justin has a success rate of John has a success rate of Visit1*10+Visit2*−5+ Visit3*10+Visit4*10+Visit5*60. Based on success rate analysis, John is connected with the current patient/provider via the connectivity protocol for discussion and follow-up treatment protocol and success rate analysis, for example.

Additionally or alternatively, these graphs are interactive. In some examples, the graph 600 includes interactive buttons and/or other indicators 608a, 608b, 608c to allow the user to interact with the graph. For example, if the user selects the interactive button 608a, the user can be provided with additional information about the steroid treatment plan; information about the success rates of previous patients (e.g., John, Mark, and Justin described above); and information about the clinicians prescribing the treatment. In other examples, the interactive button 608a can present additional analytical data, such as the data presented in FIGS. 6B, 6C, and 6D described in further detail below.

FIG. 6B includes an example graph 610 indicating example treatment success 612 for a treatment plan over a time period 614. For example, the graph 610 tracks success rate for patients 616a, 616b, 616c, 616d during the course of treatment. In some examples, the success rate is measured based on health information provided by health trackers. In the illustrated example of FIG. 6B, an overall success rate 618 is included to generate an average success rate for the patients 616a, 616b, 616c, 616d.

In the illustrated example of FIG. 6B, the first patient 616a experienced a successful treatment for a short time period 614. However, the third patient 616c underwent a longer treatment plan duration. FIG. 6B also shows that the fourth patient 616d experienced a high success rate in the beginning of the treatment, but the success rate dropped over the time period 614. In the illustrated example of FIG. 6B, the user can see that, for an example treatment plan, the overall success rate 618 is effective but may yield diminished returns over extended time periods 614.

FIG. 6C includes an example graph 620 comparing a success rate 622 over a time period 624 for more refined data. For example, the illustrated graph 620 compares the success rate 622 for the same treatment plan that was administered by different clinicians. In other examples, the graph 620 can compare different treatment plans administered by the same clinician, or different treatment plans administered by different clinicians.

In the illustrated example of FIG. 6C, first data 626a of the first treatment plan administered by the first clinician is more successful over the time period 624 than the second data 626b of the first treatment plan administered by the second clinician. However, the graph 620 also indicates the second data 626b has a higher success rate earlier in treatment. The differences between the success rate 622 of the data 626a, 626b could be the result of different dosages prescribed, for example. As a result, a user can select the first clinician to administer the first treatment plan for better long term results, or the user can select the second clinician to administer the first treatment plan for quicker short term results and slightly less successful long term results.

Figure 6D:
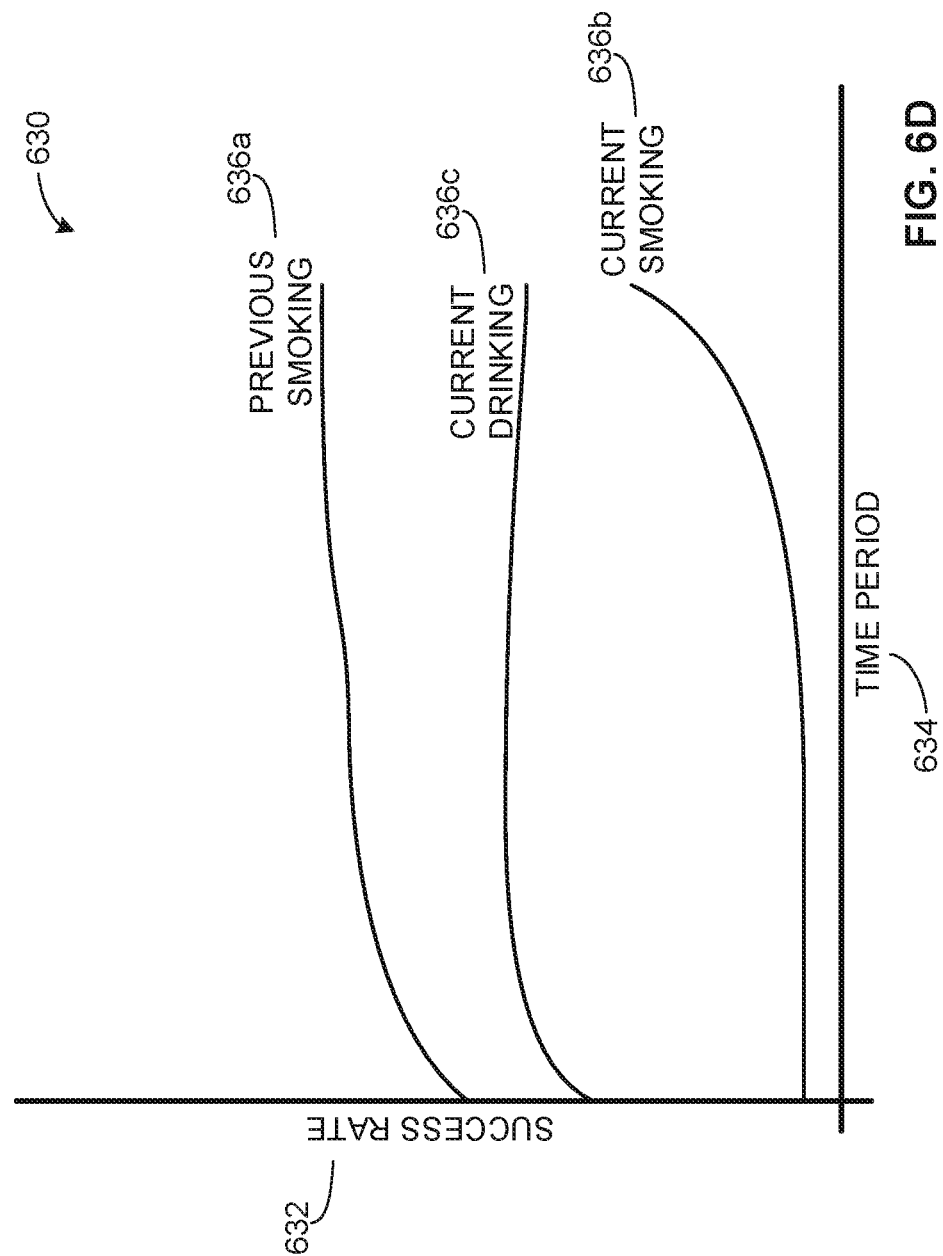

FIG. 6D includes an example graph 630 comparing success rate 632 for a treatment plan over a time period 634 based on health factors 636a, 636b, 636c. In the illustrated example of FIG. 6D, the health factors 636a, 636b, 636c include previous smoking 636a (e.g., previous tobacco smokers), current smoking 636b (e.g., current tobacco smokers), and current drinking 636c (e.g., current alcohol consumers). Additionally or alternatively, the graph 630 can include more or fewer health factors than shown.

Based on the example graph 630 of FIG. 6D, patients that have the health factor of previous smoking 636a have the highest success rate 602. Alternatively, as illustrated in the example of FIG. 6D, the patients that have the health factor of current smoking 636b have a delayed and lower success rate 602. As a result, the patient that has the health factor of current smoking 636b may be encouraged to quit smoking to improve the success rate 632 of the treatment plan.

As illustrated in FIGS. 6B, 6C, and 6D, the interactive buttons and/or other indicators 608a, 608b, 608c of FIG. 6A can be used to display additional information concerning the selected treatment plan. Additionally or alternatively, other graphs can be generated to inform the user about the success rate of the selected treatment plans. In other examples, the graphs 610, 620, 630 can be generated to display complication rates for the treatment plan instead of success rates.

FIG. 6E is an example graph 640 of treatment success rates 642 over a time period 644. For example, the graph 640 includes treatment plans 646a, 646b, 646c that have different success rates 642 and span different time periods 644. In some examples, the graph 640 can include more or fewer treatment plans. Additionally the treatment plans 646a, 646b, 646c include interactive buttons and/or other indicators 648a, 648b, 648c respectively. For example, the interactive buttons 648a, 648b, 648c present additional information about the treatment plans 646a, 646b, 646c and are similar to the interactive buttons 608a, 608b, 608c of FIG. 6A. In some examples, the graph 640 can replace or be presented alongside the graph 600 of FIG. 6A.

In the illustrated example of FIG. 6E, the first treatment plan 646a has a long treatment time period 644 and moderately successful treatment success rate 642. Alternatively, the example second treatment plan 646b has a short treatment time period 644 and a higher treatment success rate 642 compared to the first treatment plan 646a. As a result, the user of the patient healthcare interaction device 102 can choose the second treatment plan 646b due to its high success rate 642 and short treatment time period 644.

Figure 6F:
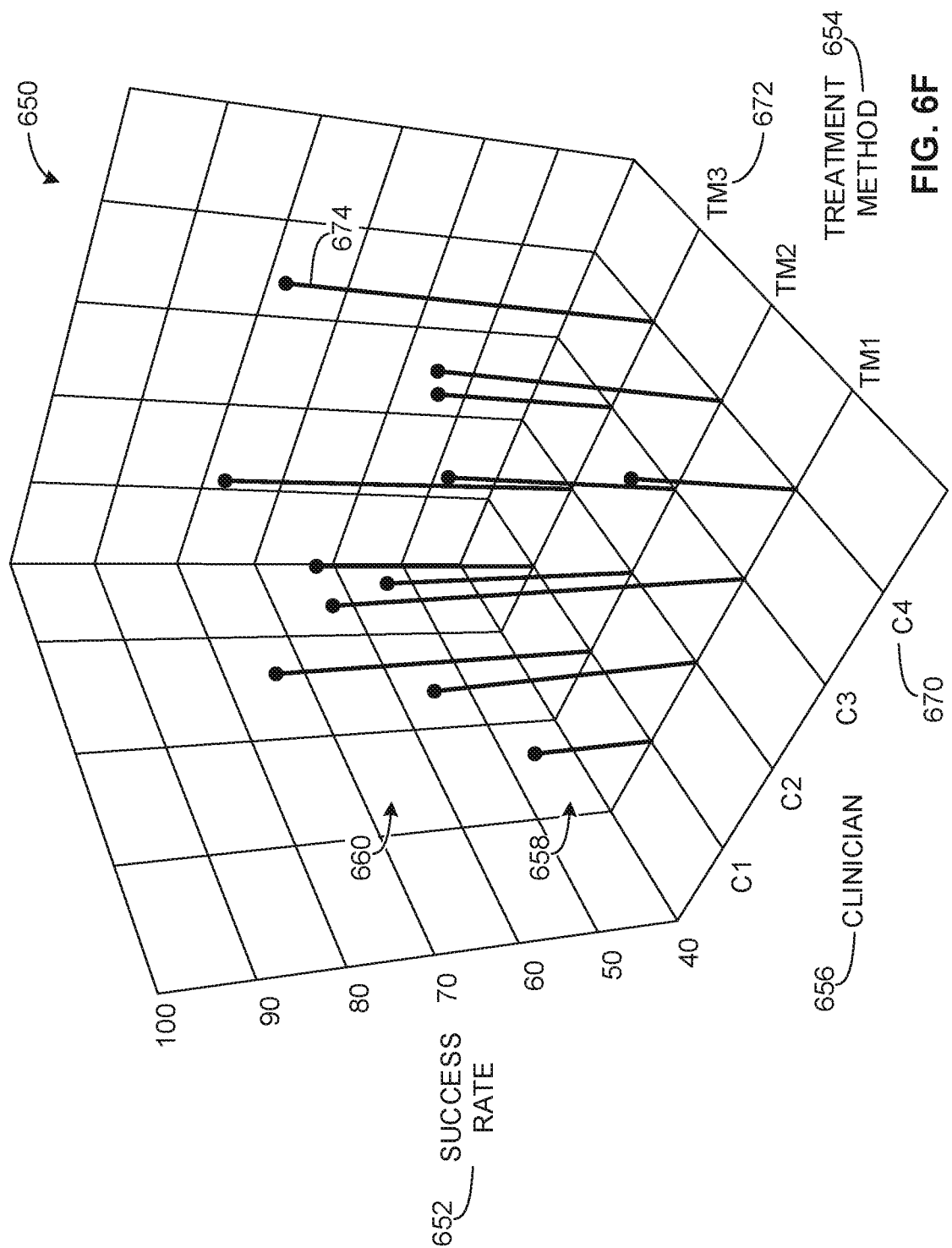

FIG. 6F illustrates an additional example success rate graph 650 for displaying success rates 652 of treatment methods 654 corresponding to respective clinicians 656. In some examples, the graph 650 can be rotated to view the graph 650 from different angles. Additionally or alternatively, the graph 650 can be presented in lieu of or alongside the graph 600 of FIG. 6A. In some examples, the treatment success data 658 include interactive buttons and/or other indicators 660. The interactive buttons 660 can be used to provide additional data concerning the treatment plans similar to the interactive buttons 648a, 648b, 648c of FIG. 6E and/or the interactive buttons 608a, 608b, 608c of FIG. 6A.

In the illustrated example of FIG. 6F, the graph 650 presents treatment success data 658 for a particular clinician 670 and a particular treatment plan 672. For example, the treatment success data 674 presents success data for the particular clinician 670 and the particular treatment plan 672. As a result, in the example of FIG. 6F, the treatment success data 674 can be differentiated from the rest of the treatment success data 658. Additionally or alternatively, other graphical displays can be generated to convey treatment success data 658.

Figure 7:
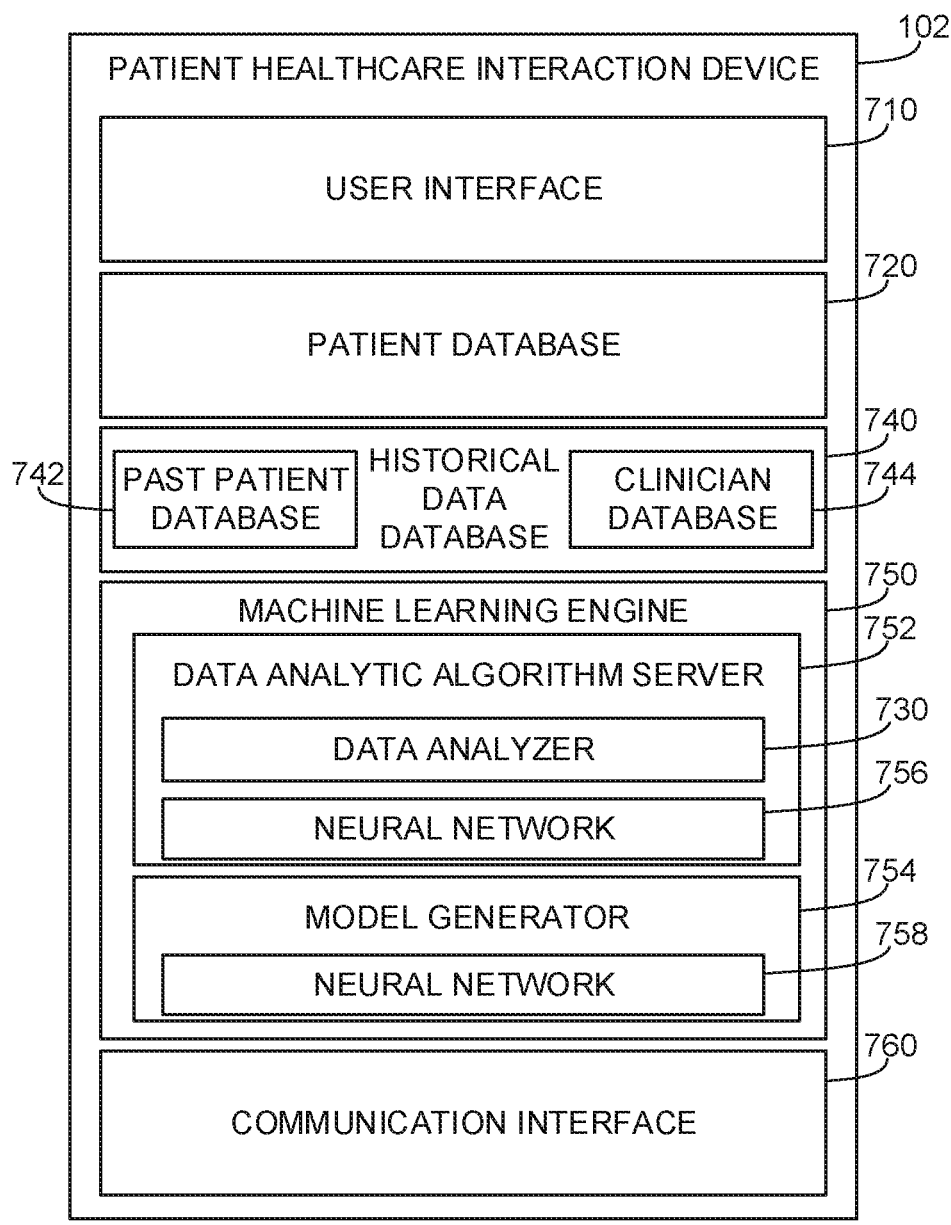
FIG. 7 is a block diagram of an example patient healthcare interaction device implemented in the system of FIG. 1.

FIG. 7 is a block diagram of an example implementation of the patient healthcare interaction device 102. In some examples, the patient healthcare interaction device 102 is implemented as its own system, however, in other examples, the patient healthcare interaction device 102 is implemented in connection with other diagnosis, treatment, and medical scheduling systems.

In the illustrated example of FIG. 7, the patient healthcare interaction device 102 includes a user interface 710. The example user interface 710 can interface with the example patient 104 of FIG. 1 and/or the example clinician 106 of FIG. 1 via a web browser, computer application, or a mobile application. For example, the user interface can be a graphical user interface (GUI) or a text based user interface (TUI). The example patient healthcare interaction device 102 receives patient information via the user interface 710.

In some examples, the patient information the user interface 710 receives is stored in a patient database 720. In some examples, the patient database 720 includes the health information 110 of FIG. 1. Additionally or alternatively, the patient database 720 stores access to care 320, personal choices 340, and environment 350 information for the example patient 104 of FIG. 1. In other examples, the patient information is processed by a data analyzer 730 and/or a data analytic algorithm server 752 before being stored in the example patient database 720.

The example patient healthcare interaction device 102 directs the patient database 720 to send the patient information to a data analyzer 730. The data analyzer 730 accesses an historical data database 740, including a past patient database 742 and a clinician database 744, to correlate the health information, including symptoms such as psychological or physiological changes to a patient's health, etc., with past patients. In some examples, the historical data database 740 corresponds to the example historical data 120 of FIG. 1, and the past patient database 742 corresponds to the example past patient health information 122 of FIG. 1. In some examples, the information stored in the patient database 720 is transferred to the historical data database 740 after the treatment plan is completed or sufficient time has passed. Choices, next actions, and/or interaction can be narrowed and/or otherwise modified as information is learned regarding patient physiological and/or psychological illness, treatment/medication information, time-based post-treatment symptom information, treatment feedback, etc.

In some examples, the data analyzer 740 associates or dissociates the patient information with past patient information based on similarities or dissimilarities respectively, of age, sex, personal choices 340, environment 350, and other relevant factors. Additionally or alternatively, the data analyzer may associate patients with higher overall visit experience and/or success rate to improve patient connectivity and success. In some examples, unless included in the patient information by a clinician, the data analyzer 740 can generate a condition diagnosis based on the past patient information by comparing current symptoms to historical symptoms.

The example data analyzer 730 sends the patient information along with associated past patient information to a machine learning engine 750. The machine learning engine includes a data analytic algorithm server 752 and a model generator 754. In accordance with the present disclosure, the example machine learning engine 750 uses the data analytic algorithm server 752 and the model generator 754 to recommend a few (e.g., three, six, etc.), but at least one possible treatment plans via the user interface 710. Additionally or alternatively, the model generator 754 facilitates generating additional detailed analysis of a treatment plan and presents the additional information. For example, if the model generator 754 determines the patient currently smokes tobacco, but non-smokers have increases success rates, the model generator 754 can provide that additional information to improve the chance of treatment plan success.

The example data analytics algorithm server 752 of the machine learning engine 750 generates predicted treatment success rates, complication rates, and clinician success rates. For example, the data analytics algorithm server 752 generates various analytical data including the graph 600 of success rates (FIG. 6). The data analytics algorithm server 752 processes the patient data and historical patient data to calculate success rates at sub-intervals for a treatment plan. Based on the success rate at the sub-intervals, the data analytics algorithm server 752 can apply an algorithm (e.g., linear gradient descent, linear regression, etc.) to predict success rates during the course of the treatment plan.

Additionally, the example model generator 754 receives the patient health information and past patient health information from the machine learning engine 750. The model generator 754 also receives the various analytical data from the data analytic algorithm server 752, including the predicted success rates during the course of the treatment plan. Based on the provided information, the example model generator 754 creates a digital twin, such as the digital twin 230 in the virtual space 235 of FIG. 2. The example model generator 754 generates the digital twin based on the condition diagnosis and the patient information analyzed by the data analyzer 730. In some examples, the model generator 754 uses the past patient information to predict the effects of the condition and various treatments on the digital twin.

In some examples, the digital twin generated by the model generator 754 and based on the calculations and predictions of the data analytic algorithm server 752 can predict effects the condition will have on the body; side effects of treatment (e.g., nausea, drowsiness, dizziness, etc.); duration of treatment; etc. For example, the digital twin can predict such effects over time based on the predicted success rates during the course of the treatment plan. The example digital twin can predict for a given treatment what symptoms and side effects will affect the patient (e.g., in a first week of treatment body aches, nausea, headaches, tiredness are expected symptoms and dizziness are expected treatment side effects) and predict when symptoms and side effects should no longer affect the patient (e.g., in the third week of treatment, nausea and tiredness should no longer be symptoms).

Additionally or alternatively, the data analytic algorithm server 752 includes a neural network 756 and/or the model generator 754 includes a neural network 758. In some examples, the neural networks 756, 758 correspond to the neural network 500 of FIG. 5. In such examples the output layer for the neural network 756 would be the success rates calculated by the data analytic algorithm server 752, and the output layer for the neural network 758 would be the example digital twin. For example, the neural network 756 receives input data from the data analyzer 730. The example neural network 756 can undergo training as a result of providing weights to connections (e.g., connections 532, 552, 572 of FIG. 5), and improve the treatment plan recommendation over time. Additionally or alternatively, the neural network 758 can be trained in an identical or similar manner.

After the example machine learning engine 750 concatenates (e.g., combines, associates, links, etc.) analytical data from the data analytic algorithm server 752 and the digital twin from the model generator 754, the example machine learning engine 750 can send the analytical data and the digital twin to the user interface 710. For example, the analytical data and the digital twin can be interacted with and manipulated by the patient 104 and/or the clinician 106 of FIG. 1. In some examples, the patient can select different health factors for the machine learning engine 750 to prioritize (described in further detail in FIG. 18). In other examples, the patient can select a subset of treatment plans to evaluate or the patient can select sub-intervals of a treatment plan time to analyze (described in further detail in FIG. 19). In some examples, the example patient 104 and/or the clinician 106 can interact with the data and the digital twin to examine the side effects and treatment success for the possible treatment plans.

In some examples, the user interface 710 includes links to past patient testimonials, such as the testimonials of previous patients 126 of FIG. 1. The example patient 104 of FIG. 1 can read this testimonials about the effects of the condition and the treatment success. In some examples, the patient healthcare interaction device 102 can facilitate anonymous communication with the past patients via a communication interface 760. For example, the communication interface 760 can include a dialog box or facilitate an anonymous phone call via the user interface 710. As a result, the patient can learn information about the possible treatment options that is difficult to quantify in the historical data database 740.

Additionally, patient information can be uploaded to the patient database 720 from a health or activity tracker or from information gathered by a clinician at subsequent medical center visits. This patient information can track the treatment plan effectiveness and/or the effect of condition symptoms or treatment side effects. In some examples, after the condition has been properly treated, the patient information, including the patient information uploaded by a health tracker, is transferred to the historical data database 740. In other examples, a condition may be incurable, and the treatment plan can only mitigate the condition symptoms. In such examples, the patient information, including the patient information uploaded by a health tracker, is transferred to the historical data database 740 after a sufficient amount of data has been collected (e.g., one month of data, four months of data, one year of data, etc.).

The example patient healthcare interaction device 102 also includes a communication interface 760. In some examples, the communication interface 760 provides anonymous communication between a patient and a past patient. For example, the communication interface 760 can generate a dialog box on the screen that does not include any personal information. In other examples, the communication interface 760 can be used for patients and clinicians to contact each other. Additionally or alternatively, the communication interface 760 can be used to help schedule an appointment with a clinician or follow-up treatment administrations.

Figure 8:
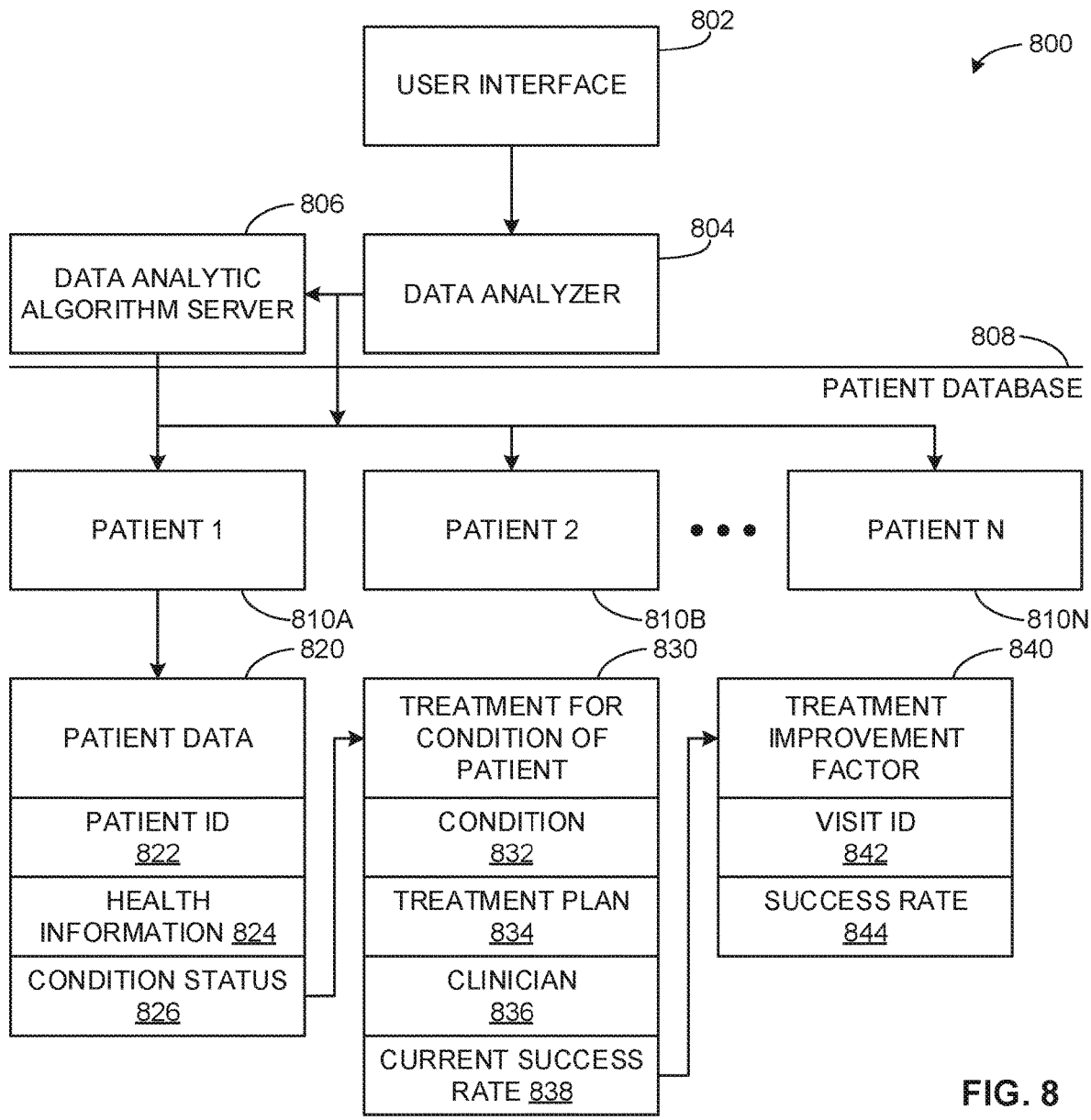
FIG. 8 is an example data structure of the example patient healthcare interaction device of FIGS. 1 and 7.

FIG. 8 is an example data structure 800 of the example patient healthcare interaction device 102 of FIGS. 1 and 7. In the illustrated example of FIG. 8, the data structure 800 is generated based on patient information received via a user interface 802 and processed by a data analyzer 804 and a data analytic algorithm server 804. Additionally or alternatively, the patient information can be processed in other ways, such as the model generator 754 of FIG. 7.

The user interface 802 receives patient information which is processed by the example data analyzer 804. The example user interface 802 can correspond to the user interface 710 of FIG. 7 and the data analyzer 804 can correspond to the data analyzer 730 of FIG. 7. The data analyzer 804 analyzes and processes the patient data for the data analytic algorithm server 806.

In some examples, both the data analyzer 804 and the data analytic algorithm server 806 can send processed patient information to a patient database 808. In some examples, the patient database 808 corresponds to the patient database 720 of FIG. 7. The example patient database 808 can store patient information for multiple patients, such as patient 1 810A, patient 2 810B, and patient N 810N. In the illustrated example of FIG. 8, only data stored for patient 1 810A is shown, however, in other examples, data for patient 2 810B and data for patient N 810N is the same or substantially similar.

The example data for patient 1 810A is stored as patient data 820. The example patient data 820 includes a patient ID 822 (e.g., the PUID), including various patient identifiers; health information 824, including patient height, weight, and vital signs; and condition status 826. In other examples, the patient data 820 can include more or fewer fields of information. Additionally or alternatively, the health information 824 includes the behavioral choices 340 of FIG. 4 and the environment 350 of FIG. 5.

The example condition status 826 of the patient data 820 includes treatment data 830. The example treatment data 830 includes condition information 832 based on the knowledge 310 of FIG. 3, treatment plan selection 834, clinician selection 836 (e.g., identified by the CUID), and current success rate 838. In some examples, the treatment data 830 can include more or fewer fields of information. The example treatment plan selection includes scheduled medical operations, prescriptions prescribed, medication dosages, etc. The example current success rate 838 includes treatment improvement factor data 840. The example treatment improvement data 840 includes a visit ID 842, including various visit identifiers (e.g., medical center ID, appointment time, visit duration, etc.) and a success rate 844. In some examples, the success rate 844 is based on patient feedback, improvement in patient vitals, clinician confidence in condition treatment, lab test results, and/or other improvement metrics. The calculation of the example success rate 844 can vary based on condition. For example, for cancer the success rate can be calculated objectively based on the amount of cancerous cells, while asthma can be calculated subjectively based on patient comfort between medical center visits.

Figure 9:
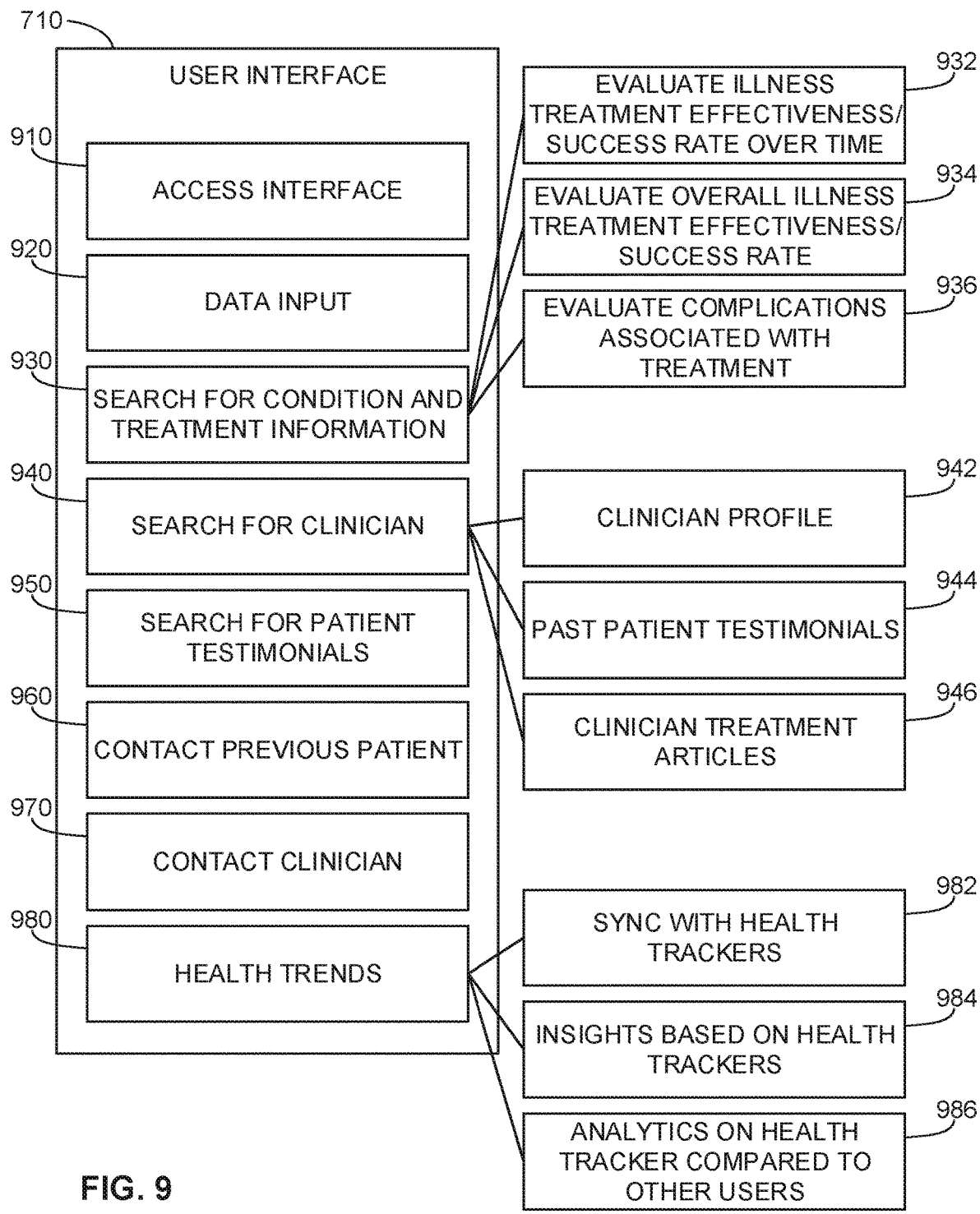
FIG. 9 is an example user interface of the example patient healthcare interaction device of FIGS. 1 and 7.

FIG. 9 is an example user interface 710 of the example patient healthcare interaction device 102 of FIGS. 1 and 7. The example user interface 710 can include a graphical user interface (GUI) displayed via a mobile device application, a web browser, or a computer program. The example user interface 710 includes an access interface 910. The example access interface 910 can guide a patient or clinician (e.g., a user) through a sign-up process and/or permit the user to login or logout of the patient healthcare interaction device 102 of FIG. 7. In some examples, after the user has signed-up, they are requested to provide patient information via a data input 920. For example, the patient information received via the data input 920 can include contact information, demographic information, etc. In some examples, the patient is provided a patient universal ID (PUID). The example PUID can be used by the patient healthcare interaction device to associate additional information with the same patient. In other examples, the data input 920 is accessed by the user to update patient information or provide new or additional information.

Additionally or alternatively, when a clinician uses the interface, the clinician logs in and provides various clinician information. For example, the clinician can provide their education, specialization, certifications, qualifications, etc. The example clinician can also provide their contact information, hospital association, and workplace address. In some examples, the clinician is provided a clinician universal ID (CUID). The example CUID can be used by the patient healthcare interaction device to associate additional information with the same clinician. In other examples, the data input 920 is accessed by the clinician to update clinician information or provide new or additional information. As information is provided with respect to the clinician (e.g., qualification and/or specialization information, location, hospital privileges, treatment information, medication information, treated patient information, etc., the clinician and/or other healthcare practitioner can be categorized, modeled, and/or otherwise processed to evaluate where and when the clinician fits for a particular patient and/or patient type's treatment, follow-up examination, etc.

Thus, a patient can leverage the interface 710 and associated backend machine intelligence which drives a plurality of technological computations and related workflows. For example, the patient can search for illness and treatment information, leveraging treatment effectiveness rate (e.g., at a point in time, over a period of time, with complications, etc.), etc., to identify treatment options, determine a provider, mine prior patient experience, and even collaborate with prior patient(s) to learn more via the interface 710. Clinician and/or other practitioner information can be provided via the interface 710 including clinician profile, articles, testimonials, health trends, etc., and the clinician can be contacted for communication via the interface 710 and beyond, for example. Health trends can be mined via the interface 710 in comparison with patient vitals, history, etc., in comparison for the particular patient, related patients, other prior patients, etc. Insights can be provided based on current and/or prior vitals for one or more measured users, for example.

In some examples, after the user has logged in, the user can use a condition search 930 to search for condition and treatment information. In the illustrated example of FIG. 9, the condition search 930 includes a segmented condition treatment evaluator 932, an overall condition treatment evaluator 934, and a treatment complications evaluator 936. For example, the evaluators 932, 934, 936 search for a condition based on health information, including symptoms such as psychological and/or physiological changes provided by the user. In some examples, the evaluators 932, 934, 936 are based only on data for the treatment effectiveness and complications. However, in other examples, the evaluators 932, 934, 936 include predictions based on the patient information that has been analyzed by the machine learning engine 750. For example, the evaluators 932, 934, 936 can include clinician notes concerning suggested reasoning for the success or failure of the treatment plan.

The example user interface 710 additionally includes a clinician search 940. For example, the clinician search 940 can present clinician profiles 942, past patient testimonials 944, treatment articles 946 written by the clinician. In some examples, the information presented in the clinician search 940 help a user select a clinician for a patient. In other examples, a user can find patient testimonials in a testimonials search 950, which can include clinician testimonials and treatment testimonials.

If, for example, a user wishes to contact previous patients or a clinician, the user can access the previous patients contact 960 or the clinicians contact 970 respectively. For example, past patients with a high success rate and/or a high overall visit experience may be recommended as patients to contact. The example previous patients contact 960 can interact with the example communications interface 760 of FIG. 7 to enable two-way anonymous communication. However, the example clinician contact 970 can interact with the example communication interface 760 of FIG. 7 to enable one-way anonymous communication.

In some examples, the user interface 710 can also include a health trends field 980. The example health trends field 980 can assist a user in tracking various health vitals. For example, the health trends field 980 can include a health tracker interface 982, a health tracker analyzer 984, and a health tracker comparator 986. The example health tracker interface 982 can allow health trackers to upload health and activity tracking into the patient healthcare interaction device 102 to improve treatment evaluation. Additionally, the health trends field 980 can provide user feedback on their health tracker activity via the example health tracker analyzer 984 and health tracker comparator 986. For example, the health tracker analyzer 984 can determine if health trends of the patient are normal. In some examples, weight gain (e.g., gain 4 kg, etc.) during a steroid treatment plan is normal and a weight loss would be abnormal. In such examples, data collected from numerous health trackers can be used to determine the normalcy of treatment side effects.

While an example manner of implementing the patient healthcare interaction device of FIG. 1 is illustrated in FIG. 7, one or more of the elements, processes and/or devices illustrated in FIG. 7 may be combined, divided, re-arranged, omitted, eliminated and/or implemented in any other way. Further, the example user interface 710, the example patient database 720, the example data analyzer 730, the example historical data database 740, the example past patient database 742, the example clinician database 744, the example machine learning engine 750, the example data analytic algorithm server 752, the example model generator 754, the example communication interface 760, and/or, more generally, the example patient healthcare interaction device 102 of FIG. 1 may be implemented by hardware, software, firmware and/or any combination of hardware, software and/or firmware. Thus, for example, any of the example user interface 710, the example patient database 720, the example data analyzer 730, the example historical data database 740, the example machine learning engine 750, the example past patient database 742, the example clinician database 744, the example data analytic algorithm server 752, the example model generator 754, the example communication interface 760, and/or, more generally, the example patient healthcare interaction device 102 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example, user interface 710, the example patient database 720, the example data analyzer 730, the example historical data database 740, the example past patient database 742, the example clinician database 744, the example machine learning engine 750, the example data analytic algorithm server 752, the example model generator 754, the example communication interface 760, and/or, the example patient healthcare interaction device 102 is/are hereby expressly defined to include a non-transitory computer readable storage device or storage disk such as a memory, a digital versatile disk (DVD), a compact disk (CD), a Blu-ray disk, etc. including the software and/or firmware. Further still, the example patient healthcare interaction device 102 of FIG. 1 may include one or more elements, processes and/or devices in addition to, or instead of, those illustrated in FIG. 1, and/or may include more than one of any or all of the illustrated elements, processes and devices.

Figure 10:
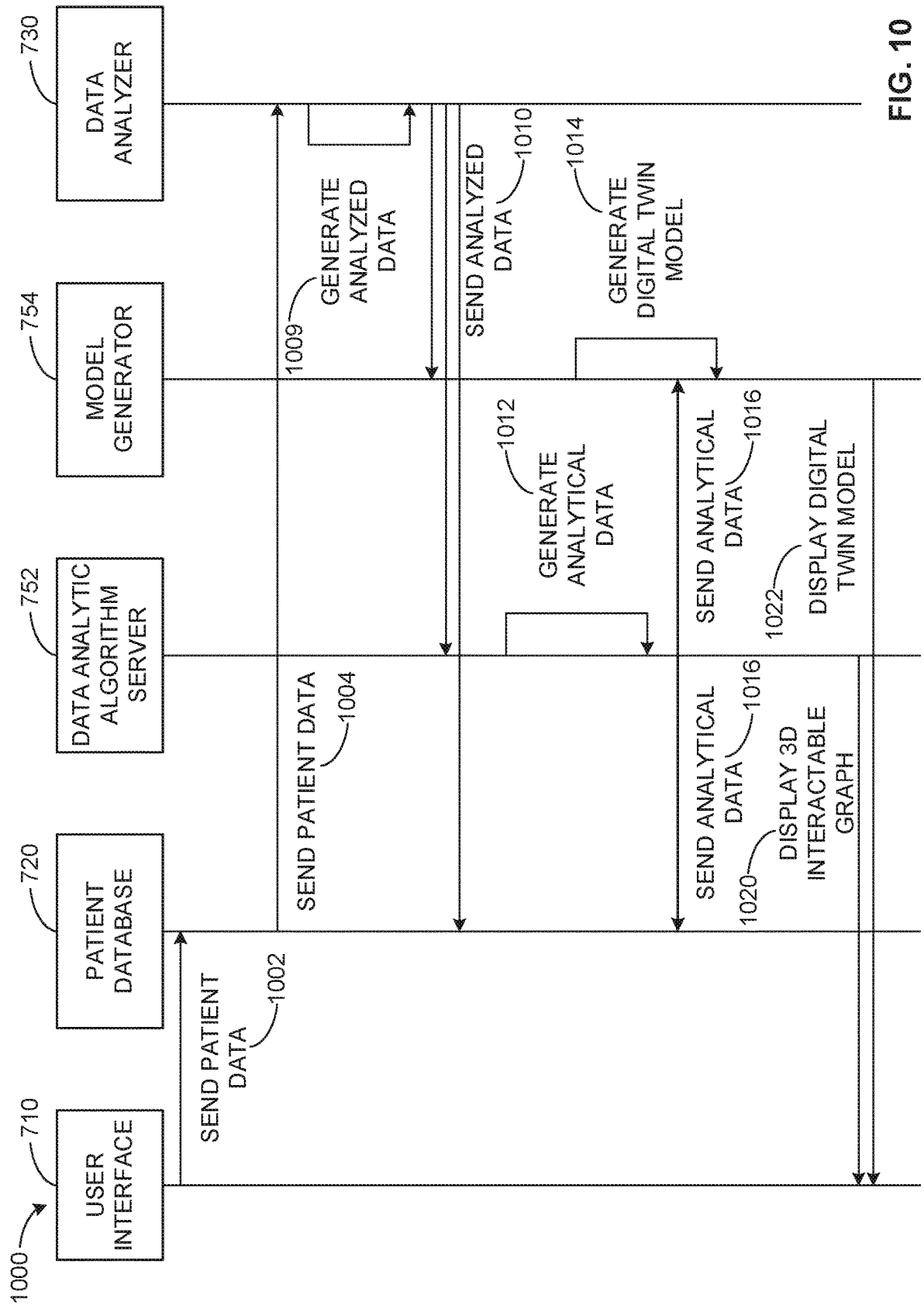
FIG. 10 is an example flow diagram of an example operation of the patient healthcare interaction device of FIGS. 1 and 7.

FIG. 10 is an example flow diagram 1000 of an example operation of the patient healthcare interaction device 102 of FIGS. 1 and 7. The data flow diagram 1000 begins when the user interface 710 of FIG. 7 receives patient data. The patient data can correspond to the health information 110 of FIG. 1 or the information stored in the patient database 720 of FIG. 7 or 808 of FIG. 8. The example user interface 710 sends the patient data 1002 to the patient database 720 of FIG. 7 which sends the patient data 1004 to the data analyzer 730 of FIG. 7.

In the illustrated example, the data analyzer 730 generates analyzed data 1009 and sends the analyzed data 1010 to the example patient database 720, the example data analytic algorithm server 752 of FIG. 7, and the model generator 754 of FIG. 7. In such an example, the patient database 720 stores the analyzed data 1010 so the analyzed data can be used for future patients as well. Additionally, the data analytic algorithm server 752 and the model generator 754, both a part of the machine learning engine 750 of FIG. 7, process the analyzed data to recommend a treatment plan.

In the illustrated example of FIG. 10, the data analytic algorithm server 752 generates analytical data 1012. In some examples, the analytical data 1012 generated by the data analytic algorithm server 752 can include, for example, overall success rates, success rates for sub-intervals of treatment duration, treatment complication rates, and clinician success rates associated with a treatment. The example analytical data can be also generated as a 3-D interactable graph.

In some examples, while the data analytic algorithm server 752 is generating the example analytical data 1012, the model generator 754 is generating a patient model 1014 such as a digital twin. In such examples, the data analytic algorithm server 752 sends analytical data 1016 before the patient model 1014 is completed. Upon receiving the analytical data 1016, the model generator 754 incorporates the analytical data 1016 into the patient model 1014. For example, the analytical data 1016 helps the patient model 1014 predict the success and complications over the course of the treatment.

In the illustrated example of FIG. 10, when the data analytic algorithm server 752 has generated the analytical data 1016 and the model generator 754 has generated the patient model 1014, the data analytical algorithm server 752 sends the analytical data as 3-D interactable graphs 1020 and the model generator 754 sends the patient model 1022 to the user interface 710. In some examples, an additional interface is provided between the data analytic algorithm server 752 and the user interface 710 and/or an additional interface is provided between the model generator 754 and the user interface 710. The additional interface(s) provides an additional level of security to protect the information of past patients and the general operation of the patient healthcare interaction device 102 by regulating access, data flow, and/or other activity through the interface, for example. For example, the interface(s) can verify, identify, authenticate an access right, and/or otherwise check permission, access rule, etc.

A flowchart representative of example machine readable instructions for implementing the patient healthcare interaction device of FIG. 1 is shown in FIGS. 12-15. In this example, the machine readable instructions comprise a program for execution by a processor such as the processor 2012 shown in the example processor platform 2000 discussed below in connection with FIG. 20. The program may be embodied in software stored on a non-transitory computer readable storage medium such as a CD-ROM, a floppy disk, a hard drive, a digital versatile disk (DVD), a Blu-ray disk, or a memory associated with the processor 2012, but the entire program and/or parts thereof could alternatively be executed by a device other than the processor 2012 and/or embodied in firmware or dedicated hardware. Further, although the example program is described with reference to the flowchart illustrated in FIGS. 12-15, many other methods of implementing the example patient healthcare interaction device 102 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, a Field Programmable Gate Array (FPGA), an Application Specific Integrated circuit (ASIC), a comparator, an operational-amplifier (op-amp), a logic circuit, etc.) structured to perform the corresponding operation without executing software or firmware.

As mentioned above, the example processes of FIGS. 12-15 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. "Including" and "comprising" (and all forms and tenses thereof) are used herein to be open ended terms. Thus, whenever a claim lists anything following any form of "include" or "comprise" (e.g., comprises, includes, comprising, including, etc.), it is to be understood that additional elements, terms, etc. may be present without falling outside the scope of the corresponding claim. As used herein, when the phrase "at least" is used as the transition term in a preamble of a claim, it is open-ended in the same manner as the term "comprising" and "including" are open ended.

Figure 11:
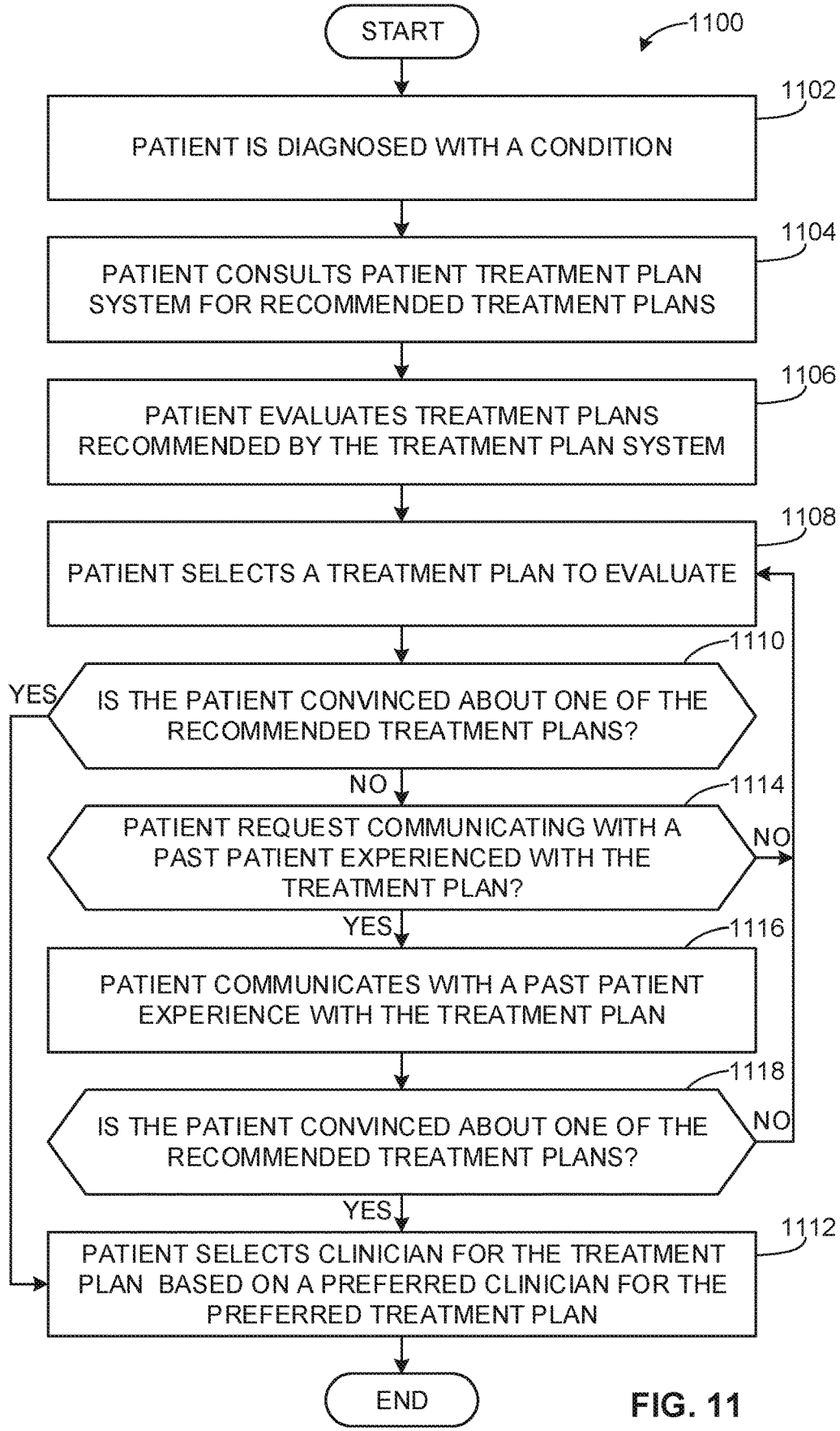
FIG. 11 is a flowchart representative of an implementation of the patient healthcare interaction device of FIGS. 1 and/or 7.

FIG. 11 is a flowchart representative of instructions 1100 for an implementation of the patient healthcare interaction device of FIGS. 1 and/or 7. The example instructions 1100 begin at block 1102. At block 1102, a patient is diagnosed with a condition. In some examples, the patient is diagnosed with the condition by a clinician. In other examples, the patient is diagnosed with the condition by the patient healthcare interaction device 102 based on historical diagnoses. After the patient has been diagnosed with the condition, the instructions 1100 continue to block 1104.

At block 1104, the patient consults the patient healthcare interaction device 102 for recommended treatment plans. For example, the patient logs into the patient healthcare interaction device 102 and provides health information, including symptoms. Based on the provided health information and symptoms, the patient healthcare interaction device 102 recommends a few (e.g., one, three, six, etc.) treatment plans. In other examples, the patient healthcare interaction device 102 already received health information, including symptoms, when the patient healthcare interaction device 102 diagnosed the patient, and the instructions 1100 continue to block 1106.

At block 1106, the patient evaluates treatment plans recommended by the patient healthcare interaction device 102. In some examples, the clinician reviews the recommended treatment plans with the patient. In other examples, the patient reviews the recommended treatments on their own. For example, the patient healthcare interaction device 102 presents four treatment options (e.g., steroids, laser treatment, surgery, and homeopathy). In some examples, the patient healthcare interaction device presents overall success rates of the presented treatment options.

As the patient evaluates the presented treatment options, the patient selects a treatment plan to evaluate in greater detail (block 1108). The patient can select the treatment plan based on personal criteria regardless of the success rate (e.g., an aversion to surgery, a preference for homeopathy, etc.). For example, when the patient selects a treatment plan to evaluate in greater detail, the patient is presented with more detailed information about the success of the treatment plan. In some examples, graphs of the success of the treatment over the duration of the treatment, probability of complication over time, and/or patient testimonials are presented. Additionally or alternatively, the patient digital twin is presented with information from the patient health trackers to verify the expected treatment condition success. In other examples, the patient digital twin can be presented alongside past patient digital twins for analysis and comparison. In such examples, the patient can activate the communication interface 760 via the digital twin to contact the past patient associated with the past patient digital twin. As a result, the patient can better analyze past patient health information and identify, in the virtual space 235, patient information concerning effects of the disease.

At block 1110, the patient determines if they are convinced about the selected treatment plan. If the patient is convinced about the selected treatment plan, the patient proceeds with the instructions 1100 of block 1112. Otherwise, the patient can further evaluate the selected treatment plan at block 1114.

At block 1114, the patient can request to communicate with a past patient. For example, they select a past patient anonymously based on a patient testimonial. If the patient decides they do not wish to request communication with a past patient, the patient returns to select a different treatment plan recommended by the patient healthcare interaction device 102 at block 1108. Otherwise, the patient proceeds to block 1116.

At block 1116, the patient communicates with a past patient. For example, the user interface generates a dialog box for anonymous communication with a past patient. In such examples, the patient can discuss the difficulties of the treatment. After the patient has communicated with the past patient, the patient continues to block 1118.

At block 1118, the patient reconsiders if they are convinced about the selected treatment plan. If the patient is still not convinced, the patient returns to block 1108 to select a different treatment plan, however, if the patient is convinced, the patient continues to block 1112.

At block 1112, the patient reviews clinicians associated with the selected treatment plan and selects a clinician. For example, a clinician could be highly recommended by past patients or the clinician could be a specialist with a high success rate for the selected treatment plan. After the patient has selected a clinician, the patient can undergo treatment. In some examples, the patient is presented a dialogue box, via the communication interface 760, to schedule an appointment with the clinician. In other examples, the patient must schedule with the clinician without the assistance of the patient healthcare interaction device 102.

Figure 12:
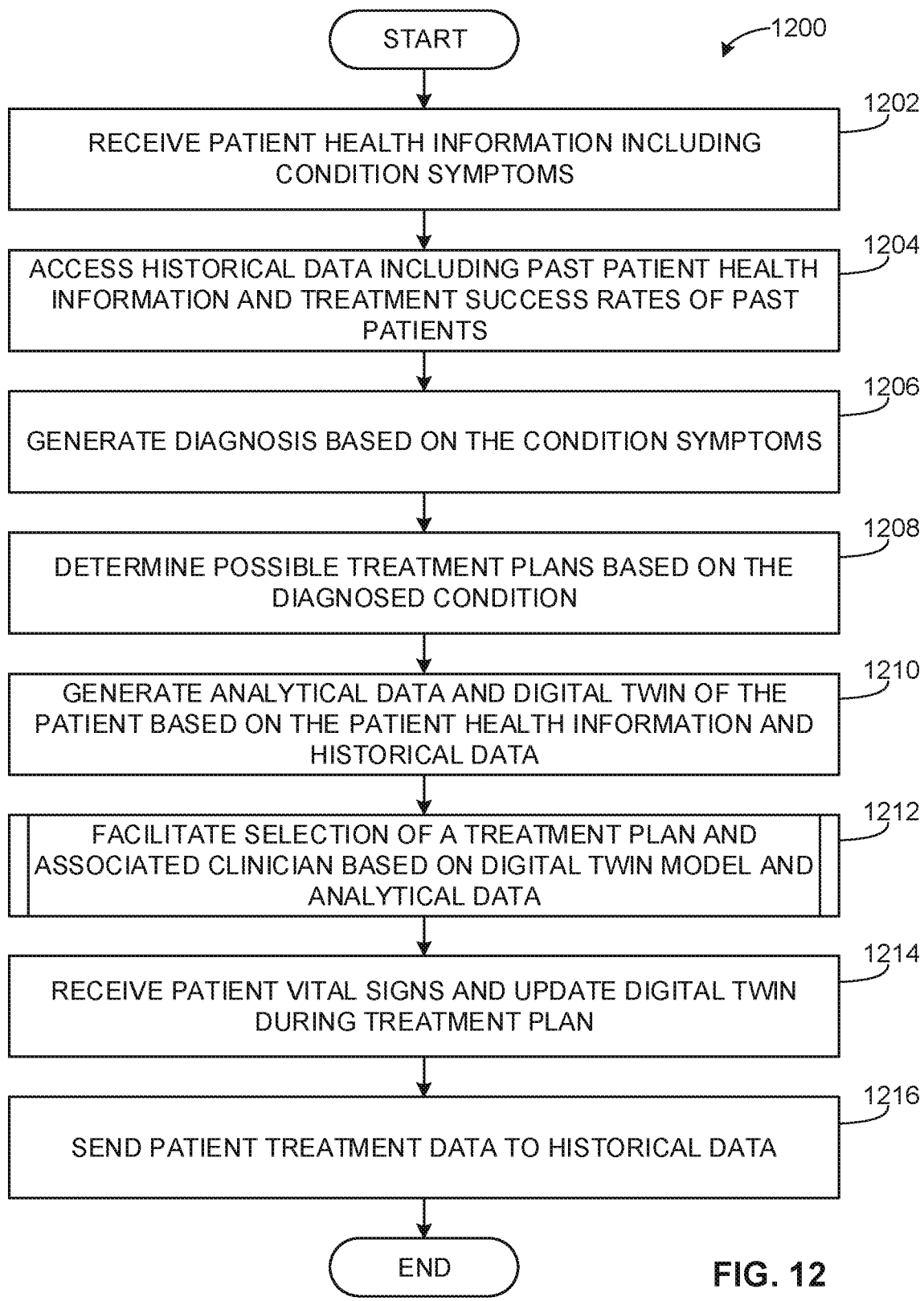
FIG. 12 is a flowchart representative of machine readable instructions which may be executed by the patient healthcare interaction device of FIGS. 1 and/or 7 for operation of the patient healthcare interaction device.

FIG. 12 is a flowchart representative of machine readable instructions 1200 which may be executed by the patient healthcare interaction device 102 of FIGS. 1 and/or 7 for operation of the patient healthcare interaction device 102. The example instructions 1200 can be performed at least in part by machine readable instructions executed by the patient healthcare interaction device 102 of FIG. 7. Additionally, in some examples, the instructions 1200 are described in connection with the example patient healthcare interaction device 102 of FIG. 7, but can, in some examples, be applicable to other medical diagnosis and treatment systems.

The instructions 1200 begin at block 1202, when the patient healthcare interaction device 102 of FIGS. 1 and 7 receives patient information. For example, the patient healthcare interaction device 102 receives patient information via the user interface 710 of FIG. 7 including sex, age, height, weight, tobacco usage, alcohol consumption, allergies, physical activity levels, and symptoms. In some examples, health information is received via the user interface based on information gathered from an examination administered by a clinician. After the health information has been received via the user interface 710, the health information is sent to the data analyzer 730 and the instructions 1200 continue to block 1204.

At block 1204, the data analyzer 730 can access historical patient information including past patient health information and treatment success rates of past patients. For example, the data analyzer 730 compares the patient health information to health information from previous patients and selects patients with similar health information (described in further detail in FIG. 18). In some examples, the data analyzer 730 also accesses the diagnosis and treatment data. After the data analyzer 730 has selected past patients with the most similar health information to the patient, the instructions 1200 continue to block 1206.

At block 1206, the data analyzer 730 generates a condition diagnosis. For example, the data analyzer compares the symptoms of the patient to the symptoms of past patients with similar health information. For example, if a patient presents symptoms of blurry vision, visual floaters, and scotomas, the data analyzer can find past patients, having those same symptoms, who were diagnosed with retinal vasculitis. Alternatively, block 1206 can be skipped if a clinician provides the diagnosis. After the patient healthcare interaction device 102 has a diagnosis, the instructions 1200 continue to block 1208.

At block 1208, the data analytic algorithm server 752 uses the patient health information, including symptoms, and past patient information, including diagnoses, to determine recommended treatment plans. For example, the data analytic algorithm server 752 can determine recommended treatment plans based on highest average success rates for a treatment, health trends for a geographic region, and information from academic journals and papers, etc. In some examples, the data analytic algorithm server 752 can limit the recommended treatment plans based on access to care 320. After treatment plans have been determined based on the patient information and historical patient information, the instructions 1200 continue to block 1210.

The machine learning engine 750 generates analytical data and a digital twin of the patient based on the patient health information and historical data (e.g., historical patient information) (block 1210). For example, the machine learning engine 750 uses the data analytic algorithm server 752 to generate analytical data including various success rates and complication rates of the possible treatment plans. Additionally, the machine learning engine 750 uses the model generator 754 and the analytical data generated by the data analytic algorithm server 752 to generate a digital model of the patient, such as the example digital twin 230 of FIG. 2.

After the patient has been provided analytical information regarding the recommended treatment plans, at block 1212, the device 102 facilitates selection of a treatment plan and an associated clinician based on the digital twin model and analytical data. The selection of a treatment plan and clinician is discussed in further detail in FIG. 13 below. After a treatment plan and a clinician have been selected, the instructions 1200 continue to block 1214.

At block 1214, the patient healthcare interaction device 102 receives patient vital signs via the user interface 710. In some examples, the patient healthcare interaction device 102 receives updated vitals based on information gathered during additional visits to a health clinic or hospital. Additionally or alternatively, the patient healthcare interaction device 102, via the example user interface 710, receives health tracking information (e.g., updated vitals based on information gathered via a health tracker). In such examples, the analytical data and the digital twin are updated based on the additional information. The updated analytical data, when incorporated into the patient model and analytical data, can be used to track success of the treatment. In other examples, the updated analytical data can be used to find closer matches to past patient health information and can also be used to predict complications that may be likely to occur.

When condition treatment is completed as determined by the patient and/or clinician, at block 1216, the patient healthcare interaction device 102 sends patient treatment data to historical data. For example, when the treatment is completed and/or the condition has passed, the data is transferred to the historical data database 740 of FIG. 7. In other examples, the condition is a chronic, incurable condition, and in such examples, the data is transferred on a regular interval. This data, although not indicative of overcoming a condition, can be used to schedule future medical center visits and the success of symptom suppression associated with the chronic condition, for example. The patient data is then, in some examples, useful in providing future recommendations.

Figure 13:
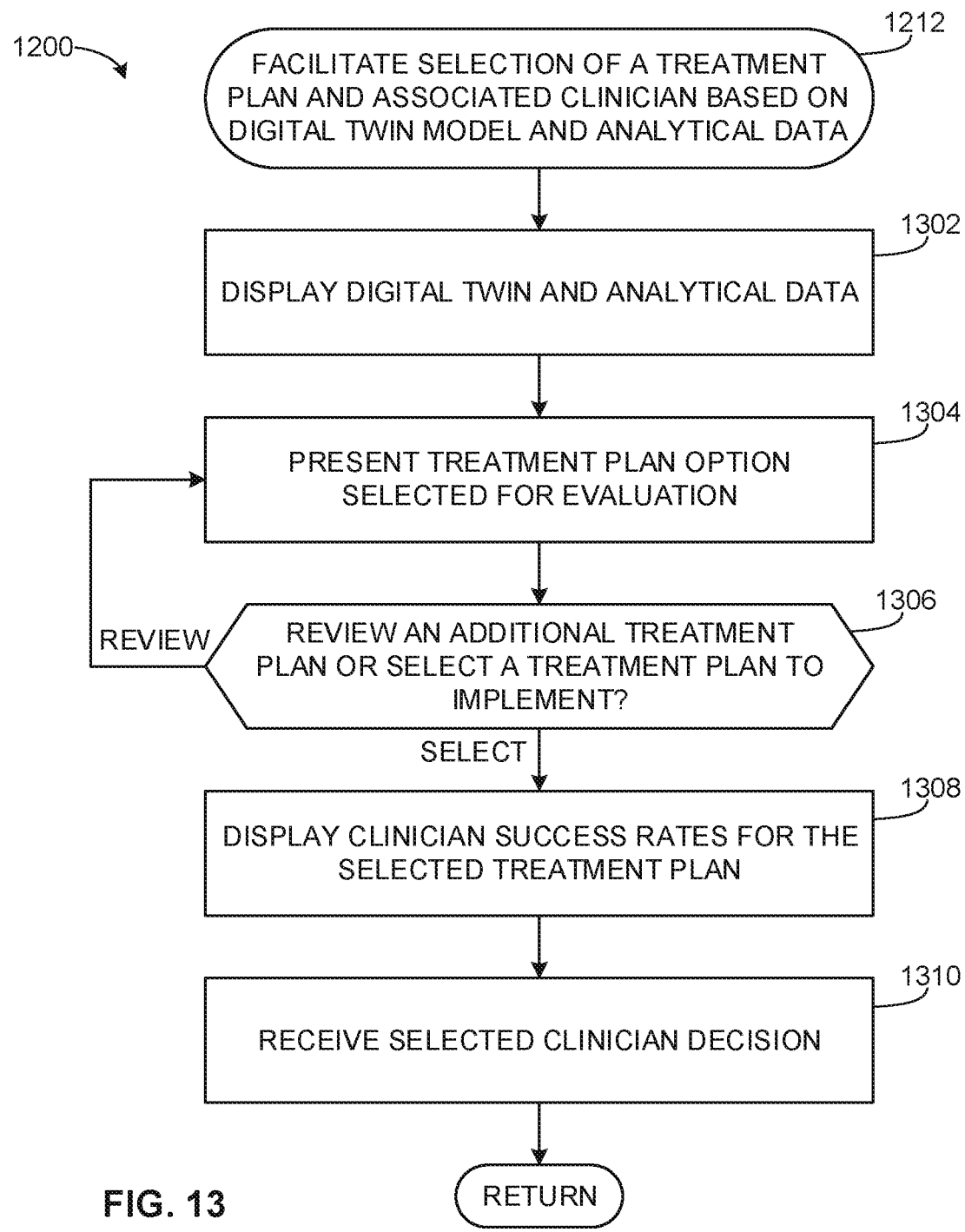
FIG. 13 is a flowchart representative of machine readable instructions which may be executed by the patient healthcare interaction device of FIGS. 1 and/or 7 for selecting a treatment plan.

FIG. 13 is a flowchart representative of machine readable instructions 1200 which may be executed by the patient healthcare interaction device of FIGS. 1 and/or 7 for facilitating or enabling selection of a treatment plan. The example instructions 1200 can be performed at least in part by machine readable instructions executed by the patient healthcare interaction device 102 of FIG. 7. Additionally, in some examples, the instructions 1200 are described in connection with the example patient healthcare interaction device 102 of FIG. 7, but can, in some examples, be applicable to other medical diagnosis and treatment systems.

The instructions 1200 to execute block 1212 begin at block 1302. At block 1302, the user interface 710 displays the digital twin 230 of FIG. 2 and analytical data. In some examples, the information is presented as a graphical display. In other examples, the information is presented via a text-based user interface. Additionally or alternatively, the digital twin 230 and the analytical information can be presented individually or simultaneously on the same screen.

Next, the user interface 710 receives a request to evaluate a treatment plan. For example, the user interface 710 presents a treatment plan option for further evaluation. In some examples, the user interface 710 now presents predicted success rates and complications for the duration of the treatment plan. Additionally or alternatively, the digital twin is presented such that predicted symptoms and side effects at different stages of the condition are displayed.

Additionally, the patient healthcare interaction device 102 may be able to manipulate the data based on inputs from the patient and/or clinician. For example, the data can be viewed along sub-intervals of the treatment plan.

At block 1306, another treatment plan can be reviewed or selected for administration. For example, the patient and/or device-generated confidence level might not be confident about the success of the treatment plan. If the patient decides and/or the device 102 determines to review another treatment plan, the instructions 1200 return to block 1304. However, if the patient decides and/or the device 102 determines to select the treatment plan for administration, the instructions 1200 continue to block 1308.

At block 1308, the patient healthcare interaction device 102 presents clinician success rates for the selected treatment plan via the user interface 710. In some examples, the success rate of clinicians administering the selected treatment plan are displayed. Additionally or alternatively, other clinician information can be displayed as well, including availability, cost, patient testimonials, educational history, etc. After the information about clinician has been evaluated, the instructions 1200 continue to block 1310.

The patient healthcare interaction device 102 receives a selected clinician decision (block 1310). In some examples, after the patient selects a clinician, the communication interface 760 assists the patient with scheduling an appointment with the selected clinician. In other examples, the user interface 710 displays contact information for the selected clinician. After block 1310, the instructions 1200 return to block 1214 of FIG. 12.

Figure 14:
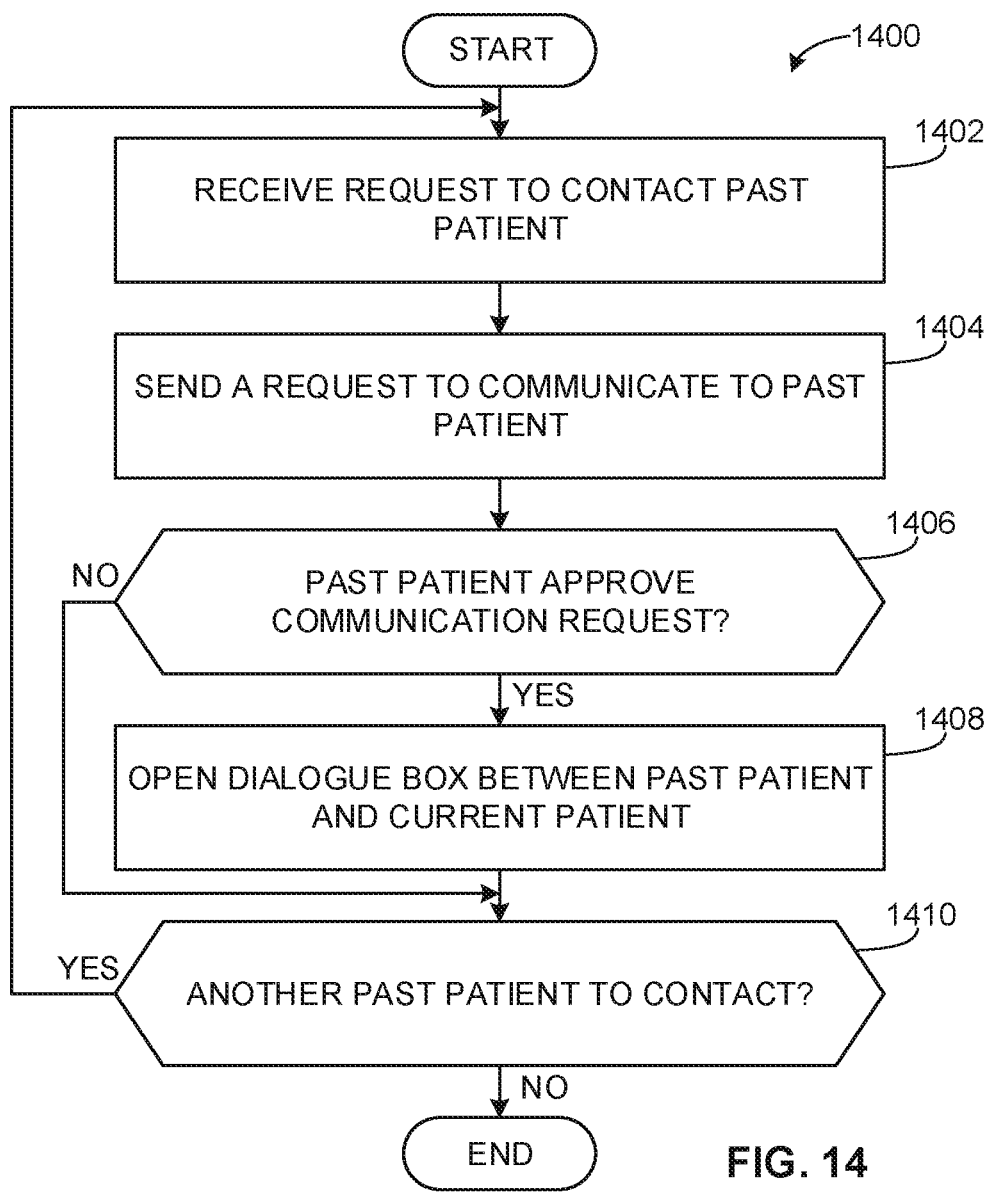
FIG. 14 is a flowchart representative of machine readable instructions which may be executed by the patient healthcare interaction device of FIGS. 1 and/or 7 for communicating with a past patient.

FIG. 14 is a flowchart representative of machine readable instructions 1400 which may be executed by the patient healthcare interaction device of FIGS. 1 and/or 7 for communicating with a past patient. Interaction can be determined and/or facilitated by machine learning analytics as described above with respect to the example of FIG. 6, for example. The example instructions 1400 can be performed at least in part by machine readable instructions executed by the patient healthcare interaction device 102 of FIG. 7. Additionally, in some examples, the instructions 1400 are described in connection with the example patient healthcare interaction device 102 of FIG. 7, but can, in some examples, be applicable to other medical diagnosis and treatment systems.

The example instructions 1400 begin at block 1402. At block 1402, the patient healthcare interaction device 102 of FIG. 1 receives a request to contact a past patient via the user interface 710 of FIG. 7. For example, the past patient may have undergone the treatment plan, may have a testimonial concerning the effects or results of a treatment plan, and/or may have a testimonial concerning the care provided by a clinician. In some examples, a past patient was recommended to the patient based on a high success rate and/or an overall visit experience for a given condition and treatment plan. After the patient healthcare interaction device 102 receives the request for contacting a past patient, the instructions 1400 continue to block 1404.

At block 1404, the communication interface 760 sends a request to communicate with the past patient. In some examples, this request can be communicated via an application on a mobile device, including a short message service (SMS) messenger, an email, a voice message, a push notification, or any hypertext transfer protocol/secure hypertext transfer protocol (HTTP/HTTPS) supported communication protocols, etc. For example, the message can be a generic, automatically generated message. In some examples, if the communication request is for a secure phone call, then the past patient can respond back with an alternative discussion time. After the request has been sent, the instructions 1400 continue to block 1406.

At block 1406, the patient healthcare interaction device 102 waits for a past patient to approve a communication request. In some examples, the communication interface 760 waits a short time (e.g., 5 minutes, 15 minutes, etc.) before cancelling the request. In other examples, the communication interface 760 waits a longer time (e.g., 2 days, 1 week, etc.) before cancelling the request. If the past patient accepts the request to communicate, the instructions 1400 continue to block 1408. However, if the past denies the request to communicate, the instructions 1400 continue to block 1410.

At block 1408, the communication interface opens a dialogue box between the past patient and current patient. The example dialogue box allows for anonymous communication between the past patient and the current patient. For example, the current patient can ask the past patient about the difficulties of any treatment side effects without either patient being able to connect the diagnosis to the identity of the other, thus retaining medical privacy. After the patients have finished communicating, the instructions 1400 continue to block 1410.

At block 1410, the patient healthcare interaction device 102 waits to determine if the patient would like to request contacting another past patient. If the patient decides to request contact with another past patient, the instructions 1400 return to block 1402. Otherwise, the patient does not want to request contact with another past patient and the instructions 1400 end.

FIGS. 15A, 15B, 15C, 15D is a flowchart representative of machine readable instructions 1500 which may be executed by the patient healthcare interaction device of FIGS. 1 & 7 to calculate various analytical data. The example instructions 1500 can be performed at least in part by machine readable instructions executed by the patient healthcare interaction device 102 of FIG. 7. Additionally, in some examples, the instructions 1500 are described in connection with the example patient healthcare interaction device 102 of FIG. 7, but can, in some examples, be applicable to other medical diagnosis and treatment systems.

Figure 15A:
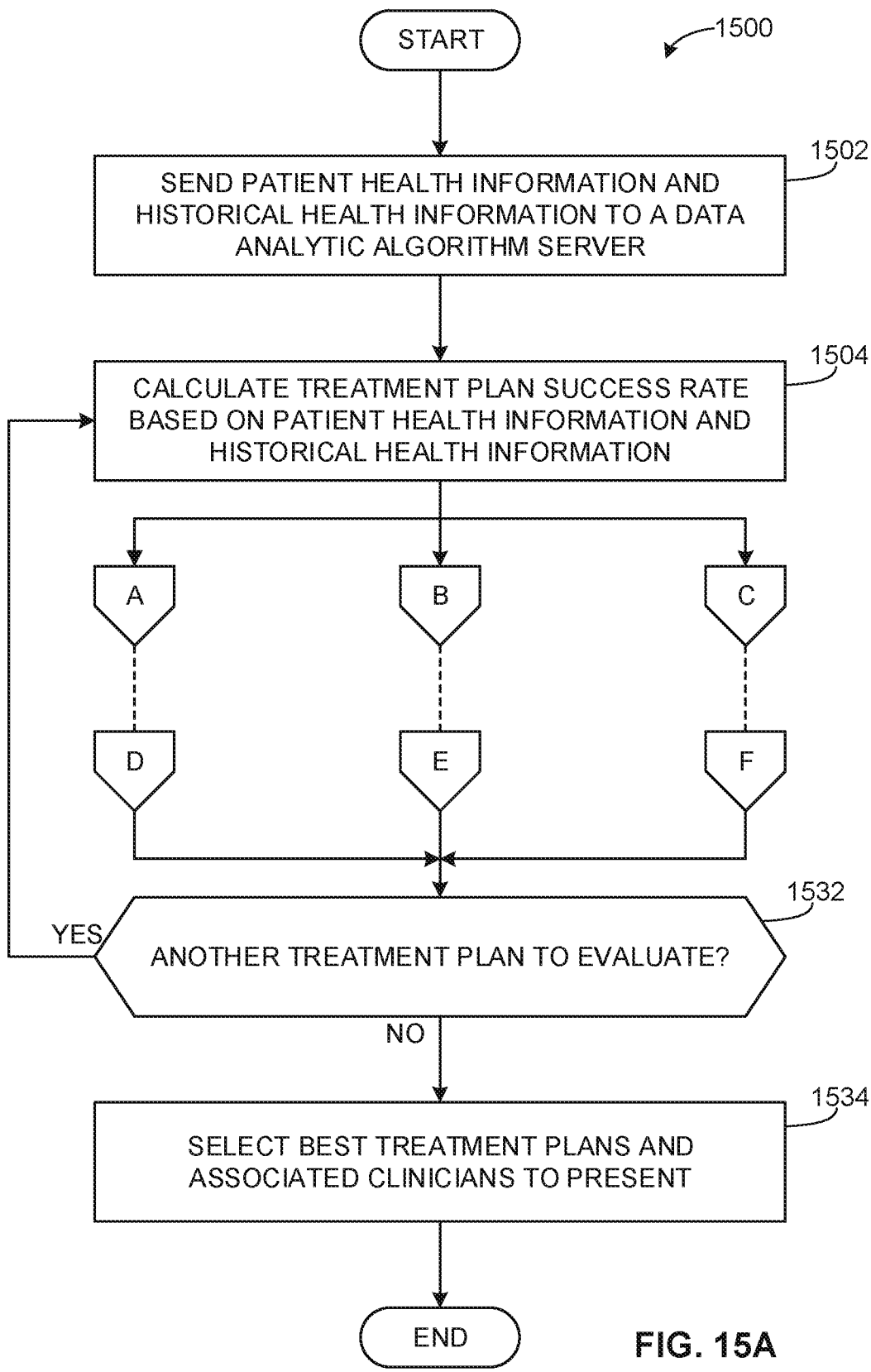
FIGS. 15A, 15B, 15C, 15D are a flowchart representative of machine readable instructions which may be executed by the patient healthcare interaction device of FIGS. 1 and/or 7 to determine analytical data.

The example instructions 1500 begin in FIG. 15A at block 1502. At block 1502, the example data analyzer 730 of the patient healthcare interaction device 102 sends patient health information and historical health information to the data analytic algorithm server 752. In accordance with the present disclosure, the example data analytic algorithm server 752 is provided all the information necessary to calculate the analytical data. After the data analytic algorithm server 752 receives the patient health information and historical health information, the instructions 1500 continue to block 1504.

The data analytic algorithm server 752 calculates the treatment plan success rate based on patient health information and historical health information (block 1504). For example, the data analytic algorithm server 752, based on the past patient health information that is similar to the patient health information, calculates success rates for possible treatment plans. In such examples, the data analytic algorithm server 752 calculates the overall success rate of the treatment plans.

Figure 15B:
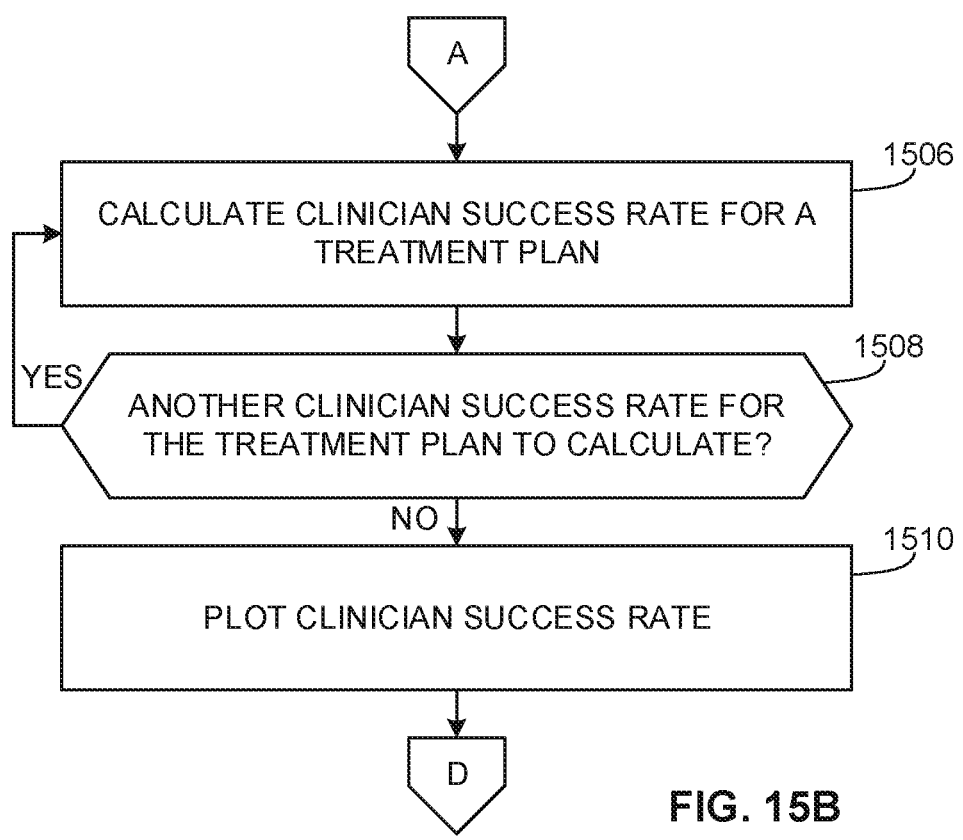

In some examples, after the data analytic algorithm server 752 calculates the success rate, the instructions 1500 proceed to block 1506 in FIG. 15B. At block 1506, the data analytic algorithm server 752 calculates a clinician success rate for a treatment plan. For example, the example clinician success rate can be calculated as a sum of successful treatments divided by a number of patients treated for the treatment plan. After the clinician success rate has been calculated for the clinician, the instructions 1500 proceed to block 1508.

At block 1508, the data analytic algorithm server 752 determines if another clinician success rate needs to be calculated. In some examples, the data analytic algorithm server 752 calculates a clinician success rate for all clinicians available to administer the treatment to the patient. If there is another clinician for whom a clinician success rate can be calculated, the instructions 1500 return to block 1506. If there are no more clinicians for whom success rates can be calculated, the instructions 1500 continue to block 1510.

At block 1510, the clinician success rate can be plotted. In some examples, the clinician success rate is a bar graph as shown in the example of FIG. 6F. In other examples, the clinician success rate is displayed in a different graphical format, such as a graph as shown in FIG. 6A or 6C. After the clinician success rate has been calculated, the example instructions 1500 continue to block 1532.

Figure 15C:
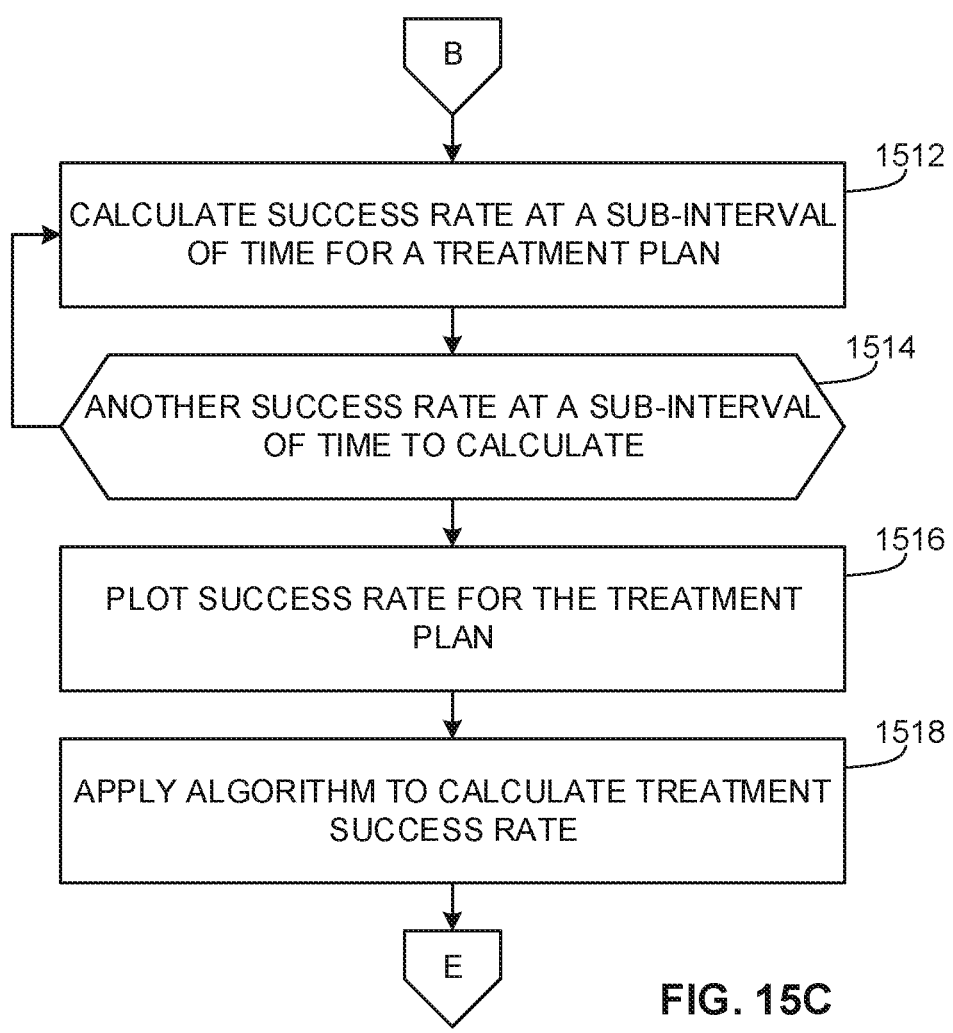

Additionally, after the data analytic algorithm server 752 calculates the success rate, the instructions 1500 proceed to block 1512 in FIG. 15C. At block 1512, the data analytic algorithm server 752 calculates a success rate at a sub-interval of time for a treatment plan. After the data analytic algorithm server 752 has calculated the success rate for a sub-interval of time, the instructions 1500 move to block 1514.

The data analytic algorithm server 752 determines if there is another success rate at a sub-interval of time to calculate (block 1514). If there are no other sub-intervals to calculate success rates for, the example instructions 1500 continue to block 1516.

At block 1516, the data analytic algorithm server 752 plots the success rate for the treatment plan. For example, the success rate is plotted as a line graph over time. Additionally, after the success rate for the treatment plan is plotted, the data analytic algorithm server 752 applies an algorithm to the plotted success rate to calculate treatment success rate (block 1518). For example, the data analytic algorithm server 752 can apply a linear gradient descent algorithm to the success rates at various sub-intervals to determine a success rate during treatment for the current patient. Additionally or alternatively, other algorithms can be used to predict the success of the treatment during sub-intervals and over the duration of the treatment plan. After the data analytic algorithm server 752 has applied the algorithm to the success rate plot, the instructions 1500 continue to block 1520.

At block 1520, the data analytic algorithm server 752 determines if another treatment plan is to be evaluated. If there is another treatment plan to be evaluated, the instructions 1500 return to block 1512. Otherwise, the instructions 1500 continue to block 1532.

Figure 15D:
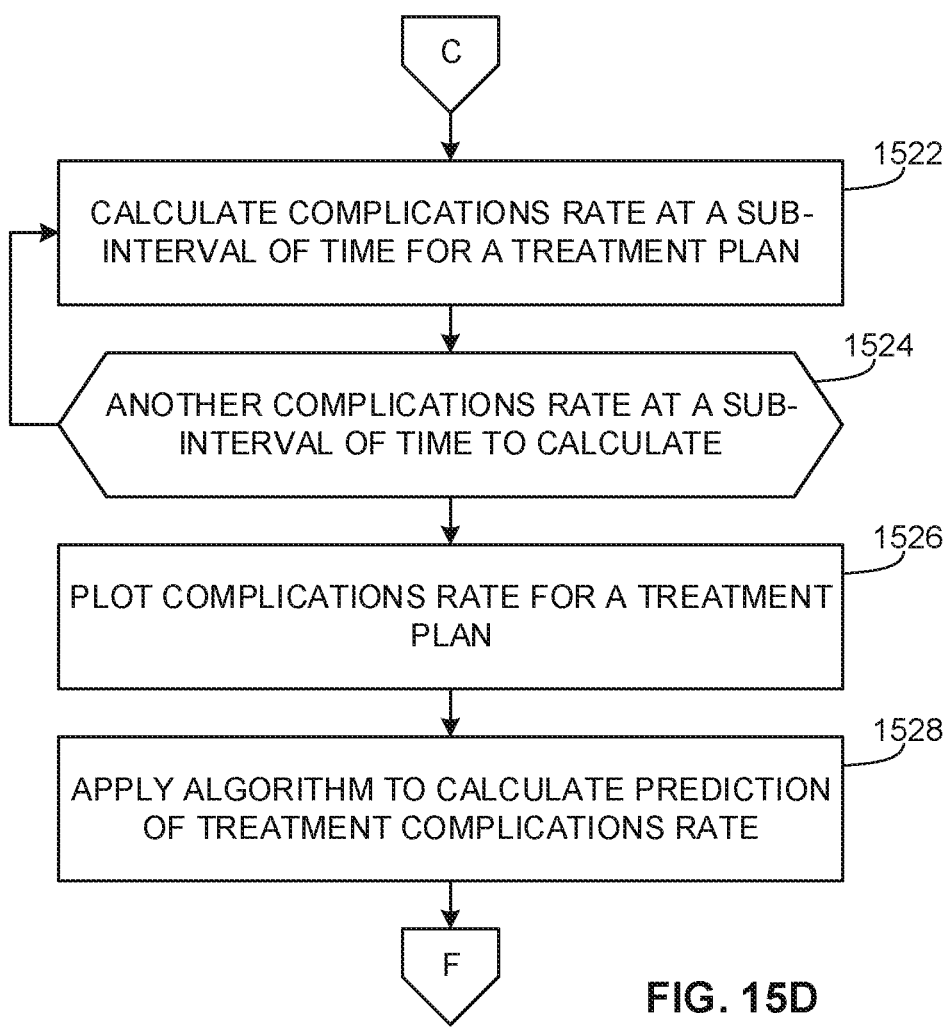

Additionally, after the data analytic algorithm server 752 calculates the complication rate, the instructions 1500 proceed to block 1522 in FIG. 15D. At block 1522, the data analytic algorithm server 752 calculates a complication rate at a sub-interval of time for a treatment plan. After the data analytic algorithm server 752 has calculated the complication rate for a sub-interval of time, the instructions 1500 move to block 1524.

The data analytic algorithm server 752 determines if there is another complication rate at a sub-interval of time to calculate (block 1524). If there are no other sub-intervals to calculate complication rates for, the example instructions 1500 continue to block 1526.

At block 1526, the data analytic algorithm server 752 plots the complication rate for the treatment plan. For example, the complication rate is plotted as a line graph over time. Additionally, after the complication rate for the treatment plan is plotted, the data analytic algorithm server 752 applies an algorithm to the plotted complication rate to calculate the complications of the treatment plan (block 1528). For example, the data analytic algorithm server 752 can apply a linear gradient descent algorithm to the complication rates at various sub-intervals to determine a complication rate during treatment for the current patient. Additionally or alternatively, other algorithms can be used to predict the complications of the treatment during sub-intervals and over the duration of the treatment plan. After the data analytic algorithm server 752 has applied the algorithm to the complication rate plot, the instructions 1500 continue to block 1532.

Returning to FIG. 15A, the data analytic algorithm server 752 determines if there is another treatment plan to evaluate (block 1532). If all treatment plans have been evaluated, the example instructions 1500 continue to block 1534. Otherwise the instructions 1500 return to block 1504 to evaluate an additional treatment plan.

At block 1534, the data analytic algorithm server 752 selects the best treatment plans and associated clinicians to present. For example, if twelve treatment plans were evaluated, only a few would be selected (e.g., three, five, etc.), but at least one treatment plan. In such examples, twelve treatment plans would be too many treatment plans for a patient to consider, so the treatment plans with the best success rate and/or least complication rate would be selected.

Figure 16:
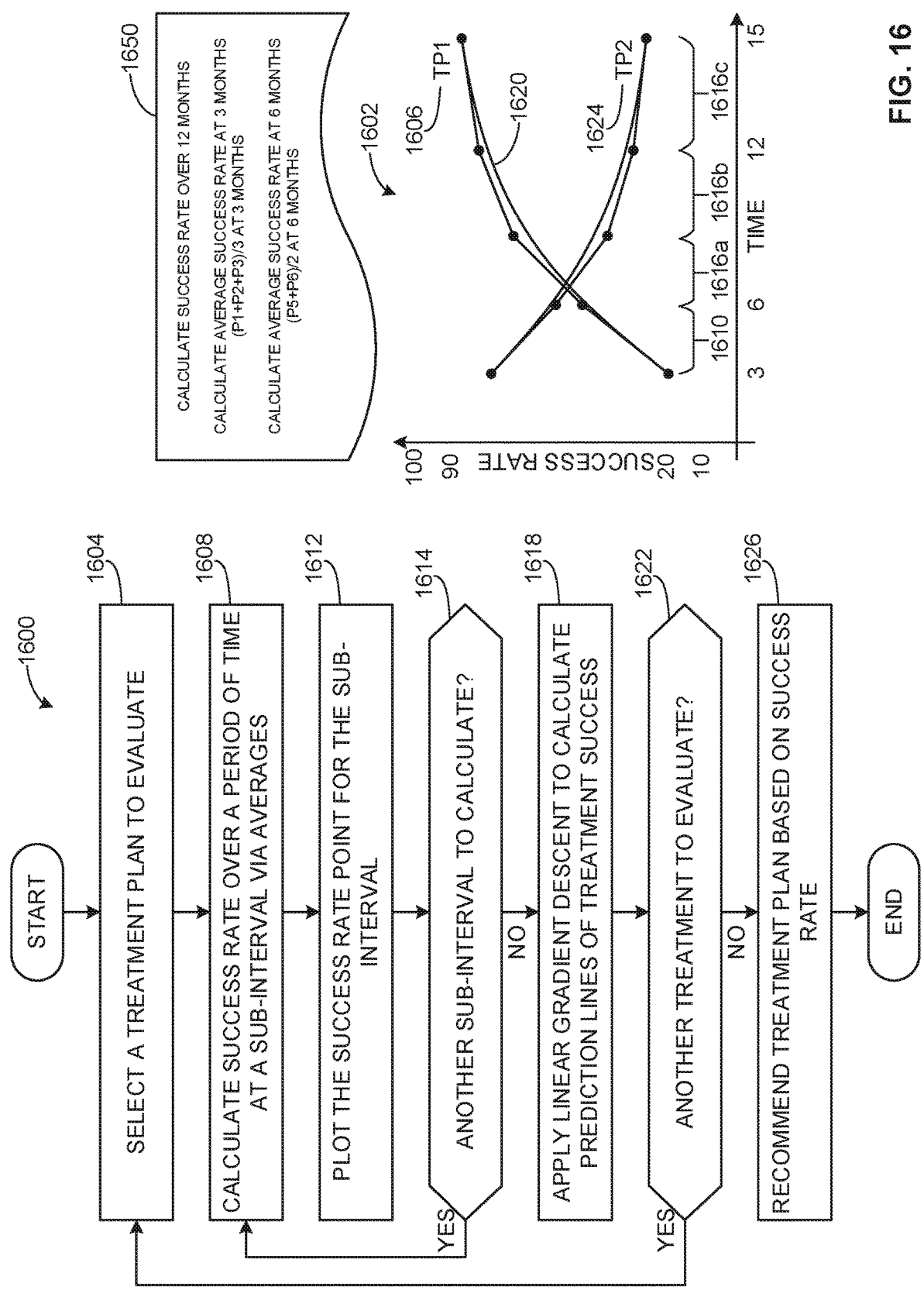
FIG. 16 is a flowchart representative of machine readable instructions which may be executed by the patient healthcare interaction device of FIGS. 1 and/or 7 for recommending a treatment plan based on success rate.

FIG. 16 is a flowchart representative of machine readable instructions 1600 which may be executed by the patient healthcare interaction device 102 of FIGS. 1 and/or 7 for generating analytical data such as the graph 1602 for recommending a treatment plan based on success rate. The example instructions 1600 can be performed at least in part by machine readable instructions executed by the patient healthcare interaction device 102 of FIG. 7. Additionally, in some examples, the instructions 1600 are described in connection with the example patient healthcare interaction device 102 of FIG. 7, but can, in some examples, be applicable to other medical diagnosis and treatment systems.

The example instructions 1600 begin at block 1604. At block 1604, the data analytic algorithm server 752 of FIG. 7 selects a treatment plan to evaluate, such as a treatment plan 1606. The selected treatment plan 1606 can be any one of the treatment plans in the historical data database 740 of FIG. 7 for treating a diagnosed condition. After the data analytic algorithm server 752 selects a treatment plan to evaluate, the instructions continue to block 1608.

The example data analytic algorithm server 752 calculates a success rate over a period of time at a sub-interval via averages (block 1608). For example, the sub-interval 1610 shows a success rate over a period of time (e.g., 3 months). In some examples, the success rate is calculated based on the factors and equations described in connection with FIG. 6. At block 1612, the data analytic algorithm server 752 plots the success rate as shown in the example graph 1602. After the success rate is plotted for the sub-interval 1610, the instructions continue to block 1614.

At block 1614, the data analytic algorithm server 752 determines if there is another sub-interval to calculate. For example, sub-intervals 1616a, 1616b, 1616c can collectively span a period of time (e.g., 1 week, 2 months, 2 years, etc.). Additionally, the sub-intervals can individually span shorter periods of time (e.g., 2 days, 2 weeks, 3 months, etc.). In some examples, there can be more or fewer sub-intervals 1610, 1616a, 1616b, 1616c than shown in graph 1602. If the data analytic algorithm server determines there are additional sub-intervals 1616a, 1616b, 1616c to calculate, the instructions 1600 return to block 1608. Otherwise, if all sub-intervals 1616a, 1616b, 1616c have been calculated, the instructions 1600 continue to block 1618.

At block 1618, the data analytic algorithm server 752 applies an algorithm to calculate prediction lines, such as a prediction line 1620, of treatment success. For example, the data analytic algorithm server 752 can apply a linear gradient descent algorithm to calculate the prediction lines. In other examples, other machine learning algorithms could be used to determine the predictions lines. In the illustrated example of FIG. 16, the prediction line 1620 indicates a likely success rate for a sub-interval (e.g., sub-interval 1610, 1616b, etc.). After the prediction line 1620 has been calculated, the instructions 1600 continue to block 1622.

The data analytic algorithm server 752 determines if there is another treatment to evaluate (block 1622). For example, if treatment plan 1606 is steroids, the example data analytic algorithm server 752 determines treatment plan 1624 (e.g., homeopathy, lasers, etc.) needs to be evaluated. If another treatment plan 1624 needs to be evaluated, the example instructions 1600 return to block 1604. In some examples there can be more treatment plans than shown in graph 1602. If there are no additional treatment plans to evaluate, the instructions 1600 continue to block 1626.

At block 1626, the data analytic algorithm server 752 recommends a treatment plan based on success rate. For example, the data analytic algorithm server 752 may recommend the treatment plan 1606, because the long-term success rate is higher than the treatment plan 1624. After the data analytic algorithm server 752 recommends a treatment plan based on success rate, the instructions end.

As illustrated in FIG. 16, the calculation 1650 of average success for a sub-interval (e.g., sub-interval 1610) is calculated by an average success rate of patients treated during the sub-interval. For example, the calculation 1650 at sub-interval 1616b includes fewer patients than sub-interval 1610. As a result, each subsequent sub-interval is calculated based on the remaining unsuccessful patients, for example.

Additionally or alternatively, the instructions 1600 can also be used to calculate a complication rate for sub-intervals of the treatment plan. In such examples, the complication rate is calculated in a similar or identical manner to success rate, however, the graph measures treatment complication rates over sub-intervals instead of treatment success rates.

Figure 17:
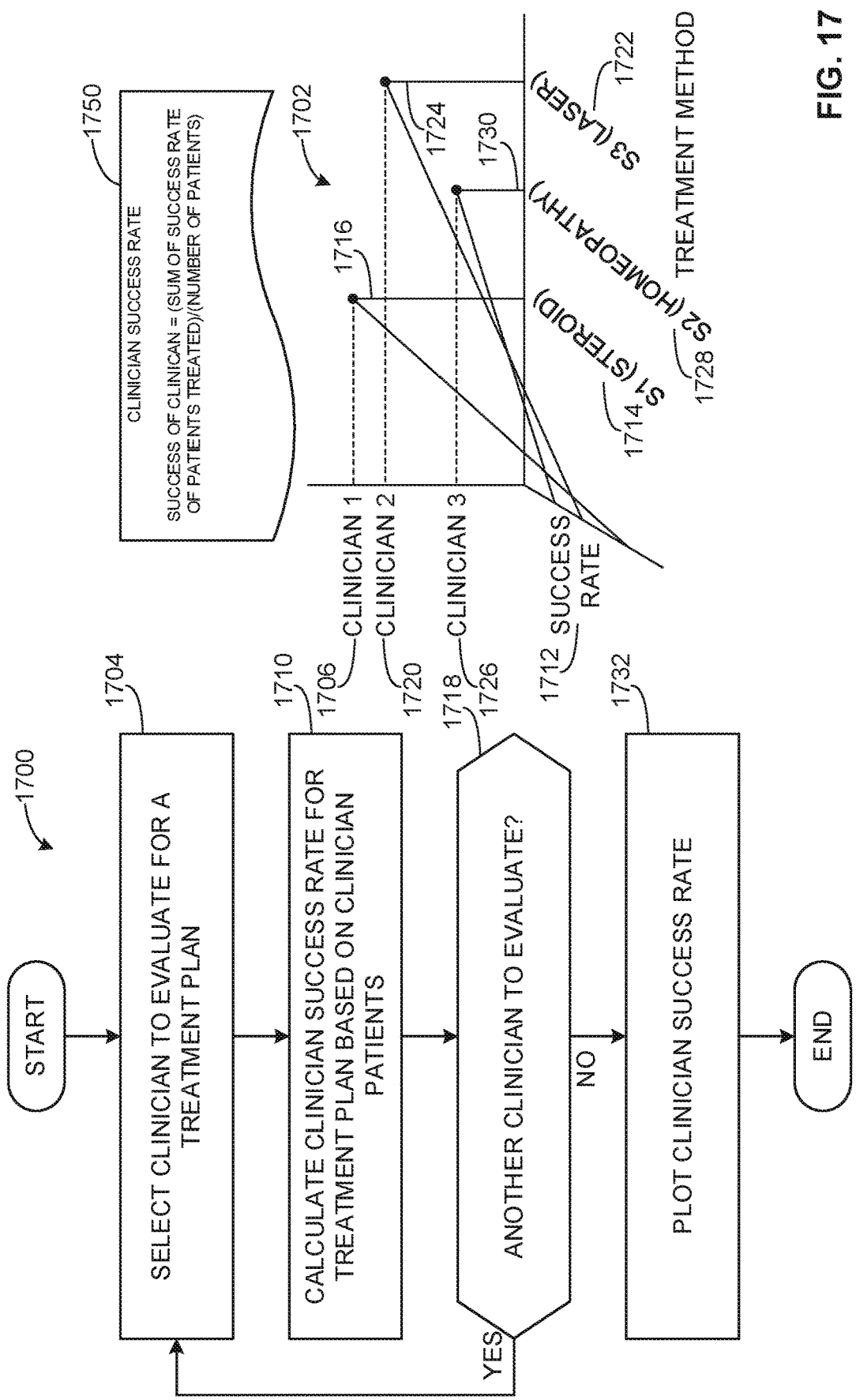
FIG. 17 is a flowchart representative of machine readable instructions which may be executed by the patient healthcare interaction device of FIGS. 1 and/or 7 for selecting a clinician based on clinician success rate.

FIG. 17 is a flowchart representative of machine readable instructions 1700 which may be executed by the patient healthcare interaction device of FIGS. 1 and/or 7 for generating a graph 1702 useful in selecting a clinician based on clinician success rate. The example instructions 1700 can be performed at least in part by machine readable instructions executed by the patient healthcare interaction device 102 of FIG. 7. Additionally, in some examples, the instructions 1700 are described in connection with the example patient healthcare interaction device 102 of FIG. 7, but can, in some examples, be applicable to other medical diagnosis and treatment systems.

The example instructions begin at block 1704. At block 1704, the data analytic algorithm server 752 selects a clinician to evaluate (e.g., clinician 1706). In some examples, the data analytic algorithm server 752 can select any clinician that has administered a treatment for a diagnosed condition. In other examples, the data analytic algorithm server 752 only selects clinicians a patient has access to, based on access to care 320 of FIG. 3. After the clinician 1706 has been selected to evaluate, the example instructions continue to block 1710.

At block 1710, the data analytic algorithm server 752 calculates a clinician success rate 1712 for a treatment (e.g., steroids 1714) based on clinician patients 1716 (e.g., number of patients treated). In the illustrated example of FIG. 17, the clinician 1706 administered a steroid treatment 1714 to a high number of clinician patients 1716 producing a high success rate 1712. After the data analytic algorithm server determines the clinician success rate 1712 for a treatment plan, the example instructions 1700 continue to block 1718.

At block 1718, the example data analytic algorithm server 752 determines if there is another clinician to evaluate. If there is an additional clinician to evaluate, the example instructions 1700 return to block 1704. For example, the data analytic algorithm server 752 can still evaluate clinician 1720 administering laser treatment 1722 on clinician patients 1724. Additionally or alternatively, the data analytic algorithm server 752 can also evaluate clinician 1726 administering homeopathy treatment 1728 to clinician patients 1730. In both examples, the data analytic algorithm server calculates the success rate 1712 for the treatment plans 1728 and the 1722. In some examples, there can be more or fewer clinicians to evaluate, or a clinician could have administered two different treatment plans. If all clinicians 1706, 1720, 1726 have been evaluated, the example instructions 1700 continue to block 1732.

At block 1732, the data analytic algorithm server 752 plots a clinician success rate. For example, the clinician success rate could be displayed as shown in graph 1702. In some examples, the calculation 1750 used to plot the success rate is determined as a sum of success rates for patients treated divided by the number of patients treated. After the data analytic algorithm server 752 plots the clinician success rate, the example instructions 1700 end.

In some examples, the patient healthcare interaction device 102 can be an automated process. For example, the patient healthcare interaction device 102 requests patient health information, and generates suggested treatment plans and clinicians without any further user input. In other examples, the user can select certain manual controls over the operation of the patient healthcare interaction device 102. For example, the user can determine which health factors are more influential in generating the digital twin and success rate data. In other examples, the user can select the granularity of the data displayed in the analytical data. In such examples, the user may be assisted by a clinician or have previous experience treating a similar condition. As a result, the manual control of the patient healthcare interaction device 102 can provide additional user collaboration that can improve the results of the selected treatment plan.

Figure 18:
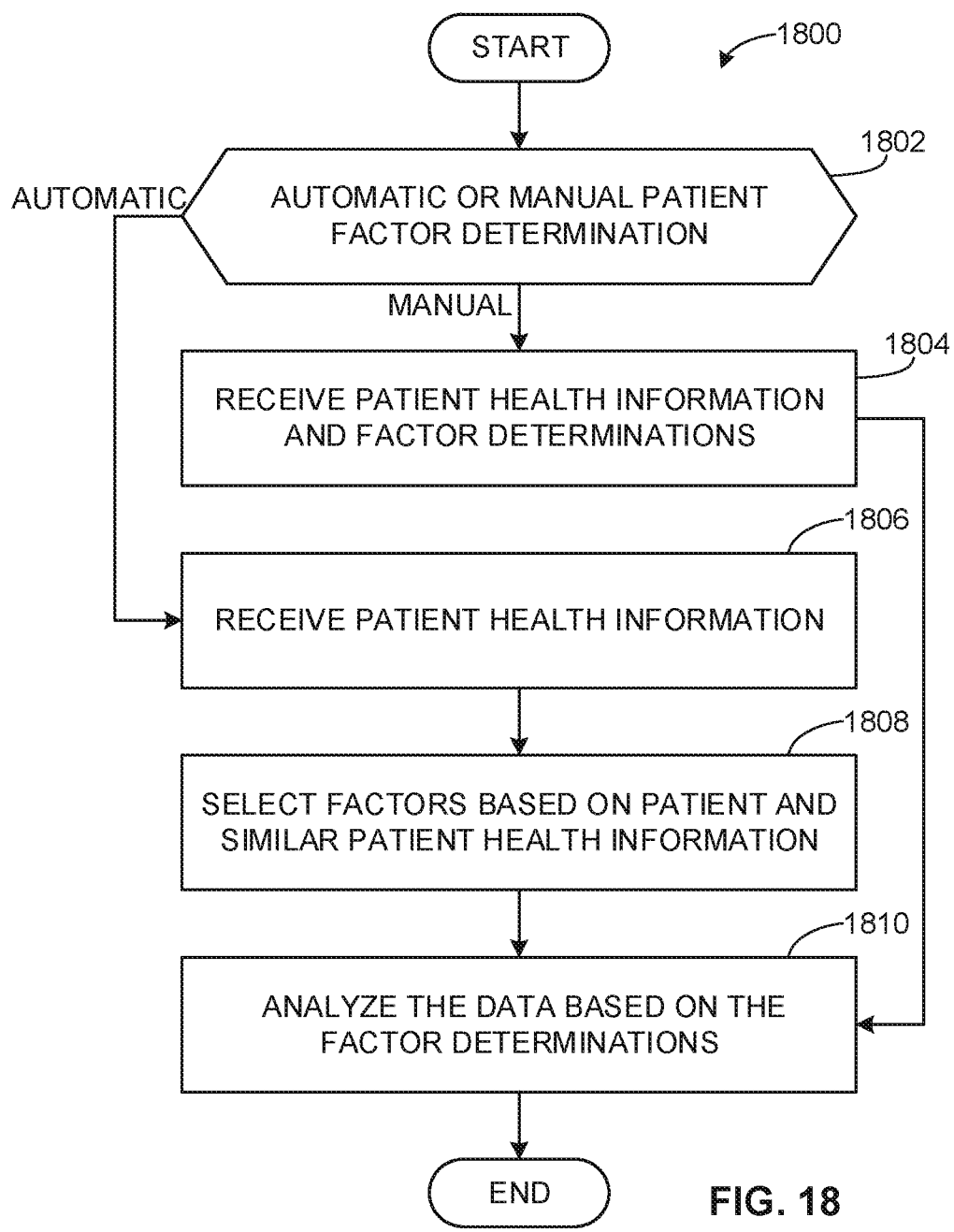
FIG. 18 is a flowchart representative of machine readable instructions which may be executed by the patient healthcare interaction device of FIGS. 1 and/or 7 for automatic or manual selection of factor determination.

FIG. 18 is a flowchart representative of machine readable instructions 1800 which may be executed by the patient healthcare interaction device of FIGS. 1 and/or 7 for automatic or manual selection of factors used by the patient healthcare interaction device 102. The example instructions 1800 can be performed at least in part by machine readable instructions executed by the patient healthcare interaction device 102 of FIG. 7. Additionally, in some examples, the instructions 1800 are described in connection with the example patient healthcare interaction device 102 of FIG. 7, but can, in some examples, be applicable to other medical diagnosis and treatment systems. In some examples, the factors can include the data of FIGS. 3, 4A, and 4B. In other examples, the factors can additionally include profession, caste, geographic area, clothing style, etc.

The example instructions 1800 begin at block 1802. At block 1802, the patient healthcare interaction device 102 receives a decision to automatically select factors or permit manual selection of factors. For example, the patient can select manual factor determination if the patient believes their diet should be given a greater weight than the data analyzer 730 of the patient healthcare interaction device 102 would normally provide for other patients. If the patient selects manual factor determination, the instructions continue to block 1804. Otherwise, automatic factor determination is selected and the instructions proceed to block 1806.

At block 1806, the patient healthcare interaction device 102 receives patient health information via the user interface 710. At block 1808, the data analyzer 730 receives the patient health information and selects factors based on patient and similar patient health information. In such an example, the data analyzer 730 determines which past patients are most similar based on predetermined factors. For example, the data analyzer 730 may use primary predetermined factors such as sex, smoking habits, and activity level, indicating these factors are important factors, but other secondary predetermined factors such as race, pets, and alcohol consumption are less important factors. As a result, in some examples, two men who smoke are more likely to be considered similar by the data analyzer than a man and a woman that both have a dog, because the two smoking men have more primary predetermined factors in common than the man and woman that have a similar secondary predetermined factor in common. In some examples, primary predetermined factors are based on the disease. For example, the dressing style of an infant patient or the mother can affect treatment for baby jaundice. In such examples, similarly dressed mothers and infants are considered more similar than differently dressed mothers and infants.

Alternatively, at block 1804, the patient healthcare interaction device can receive patient health information and factor determinations via the user interface 710. In such examples, the user determines which factors are primary factors and which factors are secondary factors. For example, a patient that does not eat any meat, may determine the vegetarian diet is a primary factor. In such examples, the patient is more likely to be considered similar to patients that have similar diets than a patient that chose automatic factor determination.

At block 1810, the data analytic algorithm server 752 analyzes the data based on the factor determinations and the model generator 754 generates the digital twin based on the data. For example, the data analytic algorithm server 752 generates the analytical data based on the similarities between the patient and the past patients determined by the factors. Additionally or alternatively, the model generator 754 generates a digital twin based on the patient health information that is similar to the past patient data from past patients that are most similar to the patient. For example, the analytical data and the digital twin are similar to past patient data for past patients that are vegetarians when the patient determines the vegetarian diet is a primary factor. In other examples, more or fewer factors may be determined to be primary factors or secondary factors.

Figure 19:
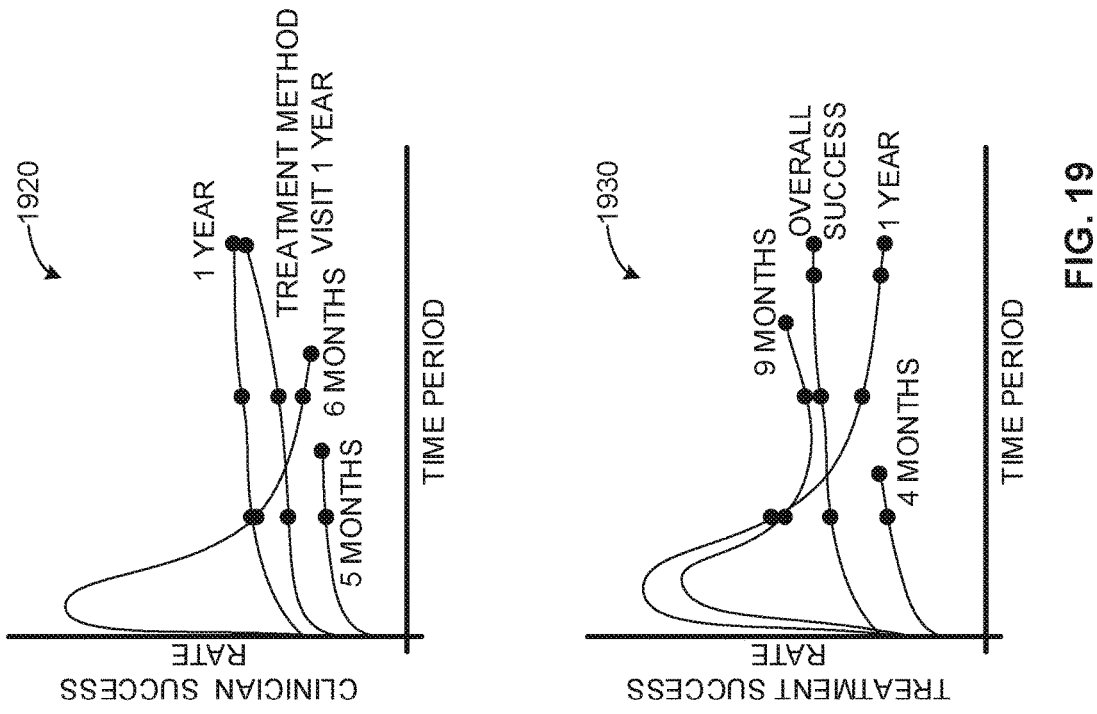
FIG. 19 is a flowchart representative of machine readable instructions which may be executed by the patient healthcare interaction device of FIGS. 1 and/or 7 for evaluating patient or treatment success at sub-intervals.
Figure 19:
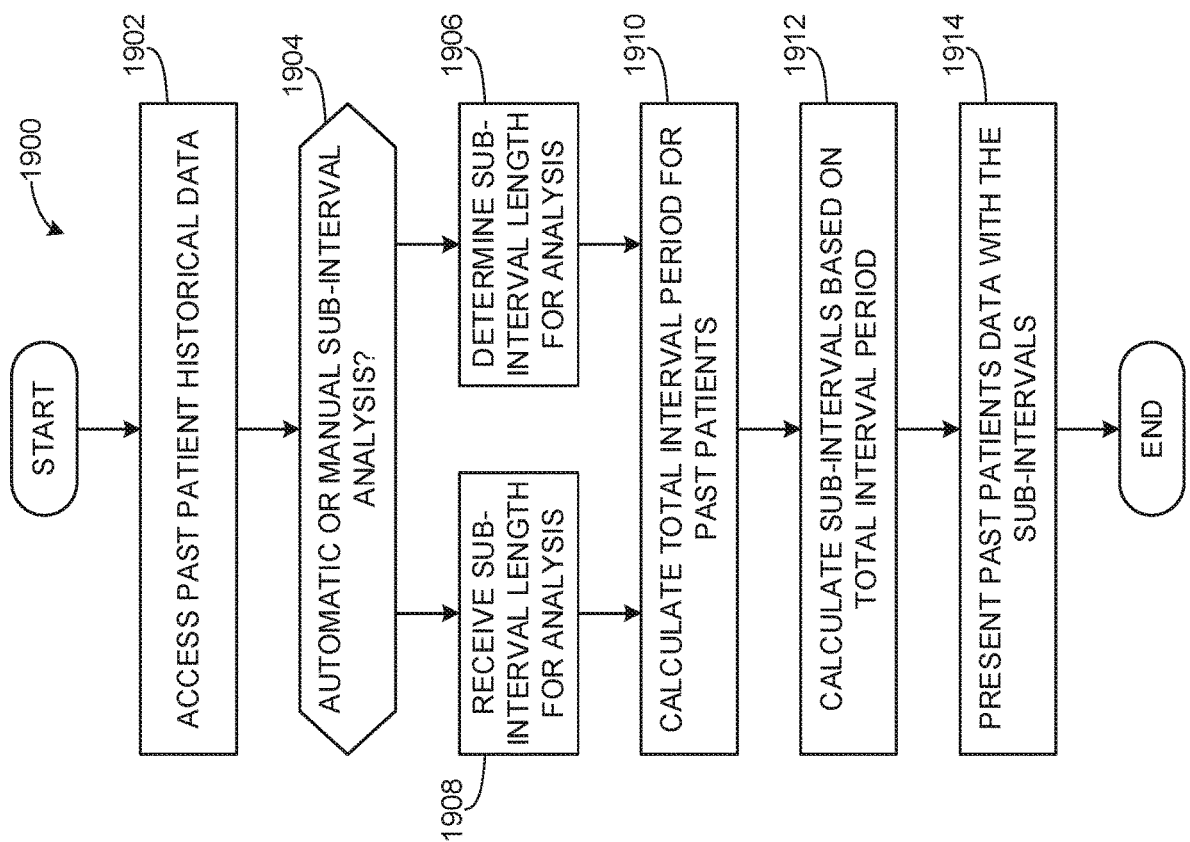

FIG. 19 is a flowchart representative of machine readable instructions 1900 which may be executed by the patient healthcare interaction device of FIGS. 1 and/or 7 for generating a clinician success graph 1920 and the treatment success rate graph 1930 useful in selecting a treatment plan. The example instructions 1900 can be performed at least in part by machine readable instructions executed by the patient healthcare interaction device 102 of FIG. 7. Additionally, in some examples, the instructions 1900 are described in connection with the example patient healthcare interaction device 102 of FIG. 7, but can, in some examples, be applicable to other medical diagnosis and treatment systems.

The example instructions 1900 begin at block 1902. At block 1902, the data analytic algorithm server 752 accesses past patient data. For example, the data analytic algorithm server 752 access data concerning the total length of treatment for past patients. At block 1904, the patient healthcare interaction device 102 receives a user selection to select a sub-interval or allow automatic sub-interval analysis.

For example, at block 1906, the data analytic algorithm server 752 determines sub-interval length for analysis based on automatic rules. In such examples, the data analytic algorithm server 752 can determine the length of sub-intervals based on predetermined rules, such as, the flu is measured in sub-intervals of 1 week. In other examples, a condition such as a broken bone may have a predetermined rule to measure the sub-intervals of 1 month. Additionally or alternatively, the sub-intervals can measure in days, multiple weeks, multiple months, and/or years.

In other examples, at block 1908, the data analytic algorithm server 752 receives a sub-interval length for analysis from the user. For example, if the patient wants a more specific time period analysis, the patient can analyze the treatment success rate in shorter intervals. This manual control can help the patient determine their expected condition for an upcoming special event or simply provide a more detailed progression of expected treatment success.

At block 1910, the data analytic algorithm server 752 calculates the total interval period for past patients. For example, the total interval is the time period from the first treatment to the completion of the treatment plan. At block 1912, the data analytic algorithm server 752 calculates the sub-intervals based on the total interval period. For example, if the total interval period is one year and the sub-interval is four months, the total interval period would be divided into three subintervals. In other examples, if the total interval is five months, the total interval period would only be divided into two sub-intervals (e.g., one four month interval and one single month interval, etc.).

At block 1914, the user interface 710 presents past patient data with the sub-intervals. For example, as shown in the example graphs 1920 and 1930, the success rate is divided into sub-intervals. In some examples, the user interface 710 can allow the patient to select a sub-interval to zoom in on and analyze in greater detail. As a result, the patient can determine their expected condition for a future date based on their selected treatment plan.

Figure 20:
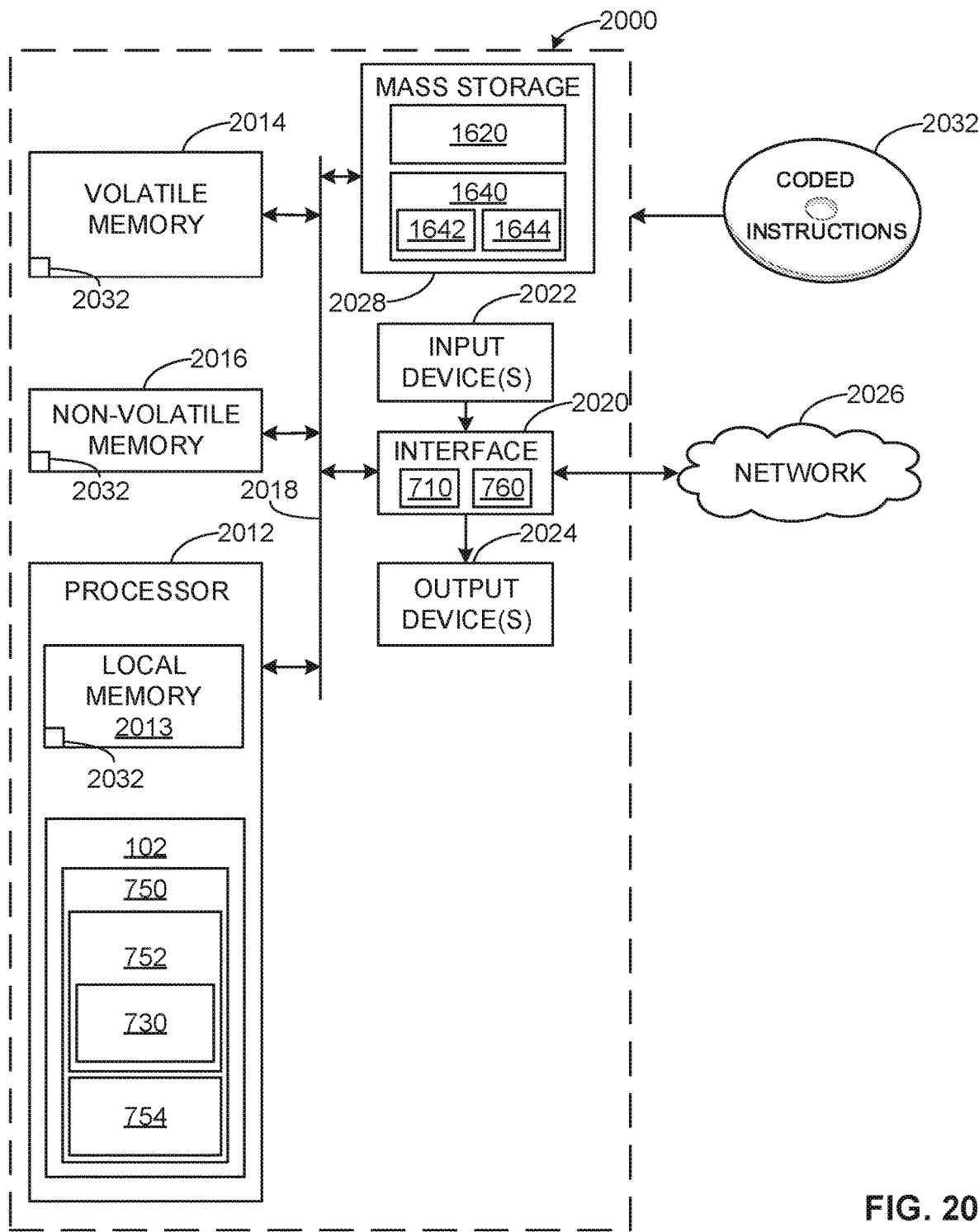
FIG. 20 is a block diagram of an example processor platform structure to execute the example computer readable instructions of FIGS. 12, 13, 14, 15A, 15B, 15C, 15D, 16, 17, 18 and/or 19 and/or implement the patient healthcare interaction device of FIGS. 1 and/or 7.

FIG. 20 is a block diagram of an example processor platform 2000 capable of executing the instructions of FIGS. 12-15 to implement the apparatus of FIG. 7. The processor platform 2000 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 2000 of the illustrated example includes a processor 2012. The processor 2012 of the illustrated example is hardware. For example, the processor 2012 can be implemented by one or more integrated circuits, logic circuits, microprocessors or controllers from any desired family or manufacturer. The hardware processor may be a semiconductor based (e.g., silicon based) device. In this example, the processor 2012 implements the example data analyzer 730, the example machine learning engine 750, the example data analytic algorithm server 752, and the example model generator 754.

The processor 2012 of the illustrated example includes a local memory 2013 (e.g., a cache). The processor 2012 of the illustrated example is in communication with a main memory including a volatile memory 2014 and a non-volatile memory 2016 via a bus 2018. The volatile memory 2014 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 2016 may be implemented by flash memory and/or any other desired type of memory device. Access to the main memory 2014, 2016 is controlled by a memory controller.

The processor platform 2000 of the illustrated example also includes an interface circuit 2020. The interface circuit 2020 may be implemented by any type of interface standard, such as an Ethernet interface, a universal serial bus (USB), and/or a PCI express interface.

In the illustrated example, one or more input devices 2022 are connected to the interface circuit 2020. The input device(s) 2022 permit(s) a user to enter data and/or commands into the processor 2012. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 2024 are also connected to the interface circuit 2020 of the illustrated example. The output devices 1024 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 2020 of the illustrated example, thus, typically includes a graphics driver card, a graphics driver chip and/or a graphics driver processor.

The interface circuit 2020 of the illustrated example also includes a communication device such as a transmitter, a receiver, a transceiver, a modem and/or network interface card to facilitate exchange of data with external machines (e.g., computing devices of any kind) via a network 2026 (e.g., an Ethernet connection, a digital subscriber line (DSL), a telephone line, coaxial cable, a cellular telephone system, etc.). In this example, the interface circuit 2020 implements the example user interface 710 and the communication interface 760

The processor platform 2000 of the illustrated example also includes one or more mass storage devices 2028 for storing software and/or data. Examples of such mass storage devices 2028 include floppy disk drives, hard drive disks, compact disk drives, Blu-ray disk drives, RAID systems, and digital versatile disk (DVD) drives.

The coded instructions 2032 of FIGS. 12-15 may be stored in the mass storage device 2028, in the volatile memory 2014, in the non-volatile memory 2016, and/or on a removable tangible computer readable storage medium such as a CD or DVD. In some examples, the mass storage also includes the example patient database 720, the example historical data database 740, the example past patient database 742, and the example clinician database 744.

From the foregoing, it will be appreciated that example methods, apparatus and articles of manufacture have been disclosed that the patient healthcare interaction device improves selection of treatment plans for diagnosed conditions and success of selected treatment plans. The portable patient healthcare interaction device improves technological delivery of healthcare and dynamic, mobile, interactive networking and connection of healthcare knowledge, best practices, patient data updates, and patient treatment. The patient healthcare interaction device, implemented as a desktop computer, laptop computer, tablet computer, smartphone, smart watch, wearable sensor, etc., provides a technologically improved healthcare monitor and healthcare wizard to guide patient and/or provider in data update, data transmission, communication, automated (e.g., artificial intelligence) clinician decision support, patient modeling, data analytics, and protocol improvement which is unobtainable and/or impractical when attempted by humans alone. Certain examples bring technological improvement to provide something significantly more than a searchable resource for healthcare information, and certain examples technologically improve data delivery, data storage, data analysis, and computer-driven determination and action.

For example, the patient healthcare interaction device suggests treatment plans that might not otherwise have been recommended to a patient based on the limited experience of a clinician the patient visits. Additionally, the patient healthcare interaction device offers information to patients undergoing treatment. In some examples, information of the difficulties of treatment plans and the success of the treatment can encourage a patient to undergo the difficulties of the treatment for the hope of the success. Additionally, the patient healthcare interaction device helps inform patients of treatment plans that have historically failed for similar patients.

It is noted that this patent claims priority from India Patent Application No. 201741046763, which was filed on Dec. 27, 2017, and is hereby incorporated by reference in its entirety.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus to select medical treatment comprising:
a user interface to receive health information for a patient, the health information including symptoms of a condition;
a data analyzer to:
   access historical patient information stored in a past patient database; and
   determine a condition based on comparing historical patient information stored in a past patient database to the health information for the patient;
a machine learning engine to recommend at least one treatment plan, to be presented by the user interface, the machine learning engine including:
   a data analytic algorithm server to determine success rates of the at least one treatment plan for the condition, the success rates based on the health information for the patient and historical health information; and
   a model generator to generate a first patient model, wherein the first patient model predicts effects of the at least one treatment plan and symptoms of the condition for a duration of the treatment plan based on the success rates; and
a communications interface to facilitate scheduling an appointment with a clinician, after the patient selects the treatment plan via the user interface;
the user interface to:
   receive health tracking information from a health tracker device associated with the patient from a network for the duration of the treatment plan, the health tracking information indicative of a treatment plan effectiveness; and
   store the health tracking information in a patient database; and
the machine learning engine to generate a second patient model based on the first patient model and the health tracking information, the second patient model to improve prediction of the effects of the at least one treatment plan and the symptoms of the condition over the first patient model, the first patient model and the second patient model representative of a digital twin of the patient that can simulate real effects on the patient in a virtual space.

2. The apparatus of claim 1, wherein the user interface is to present the success rates, the first patient model, and the second patient model.

3. The apparatus of claim 1, wherein the historical patient information includes historical health information, historical symptoms, and historical diagnoses.

4. The apparatus of claim 1, further including:
the data analyzer to associate a clinician with historical health information; and
the data analytic algorithm server to determine clinician success rates for the at least one treatment plan.

5. The apparatus of claim 1, further including a communication interface to enable communication between the patient and a past patient, wherein the past patient underwent the at least one treatment plan.

6. The apparatus of claim 1, wherein the health information is to be transferred to the past patient database when treatment is complete as determined by a clinician administering the treatment.

7. The apparatus of claim 1, wherein the model generator is to update the first patient model based on the health tracking information.

8. A computer-implemented method to select medical treatment via a patient healthcare interaction device, the method comprising:
receiving, via a user interface, health information for a patient, the health information including symptoms of a condition;
accessing, via a data analyzer, historical patient information stored in a past patient database;
determining, via a data analyzer, a condition based on comparing historical patient information stored in a past patient database to the health information for the patient;
recommending at least one treatment plan, to be presented by the user interface, by:
   determining success rates of the at least one treatment plan for the condition, via a data analytic algorithm server, the success rates based on the health information for the patient and historical health information; and
   generating a first patient model, via a model generator, wherein the first patient model predicts effects of the at least one treatment plan and symptoms of the condition for a duration of the treatment plan based on the success rates;
scheduling an appointment with a clinician, via a communication interface, after the patient selects the treatment plan via the user interface;
receiving, via the user interface, health tracking information from a health tracker device associated with the patient from a network for the duration of the treatment plan, the health tracking information indicative of a treatment plan effectiveness;
storing the health tracking information in a patient database; and
generating a second patient model, via the model generator, based on the first patient model and the health tracking information, the second patient model to improve prediction of the effects of the at least one treatment plan and the symptoms of the condition over the first patient model, the first patient model and the second patient model representative of a digital twin of the patient that can simulate real effects on the patient in a virtual space.

9. The method of claim 8, further including presenting, via the user interface, the success rates, the first patient model, and the second patient model.

10. The method of claim 8, wherein the historical patient information includes historical health information, historical symptoms, and historical diagnoses.

11. The method of claim 8, further including:
associating, via a data analyzer, a clinician with historical health information; and
determining, via a data analytic algorithm server, clinician success rates for the at least one treatment plan.

12. The method of claim 8, further including enabling, via a communication interface, communication between the patient and a past patient, wherein the past patient underwent the at least one treatment plan.

13. The method of claim 8, further including transferring the health information to the past patient database when treatment is complete as determined by a clinician administering the treatment.

14. A non-transitory computer readable storage medium comprising computer readable instructions to select medical treatment, that, when executed, cause a processor to at least:
receive health information for a patient, the health information including symptoms of a condition;
access historical patient information stored in a past patient database;
determine a condition based on comparing historical patient information stored in a past patient database to the health information for the patient;
recommend at least one treatment plan, to be presented by a user interface, based on the instructions further causing the processor to:
determine success rates of the at least one treatment plan for the condition, the success rates based on the health information for the patient and historical health information; and
generate a first patient model, wherein the first patient model predicts effects of the at least one treatment plan and symptoms of the condition for a duration of the treatment plan based on the success rates;
facilitate scheduling an appointment with a clinician, after the patient selects the treatment plan via the user interface;
receive health tracking information from a health tracker device associated with the patient from a network for the duration of the treatment plan, the health tracking information indicative of a treatment plan effectiveness;
store the health tracking information in a patient database; and
generate a second patient model based on the first patient model and the health tracking information, the second patient model to improve prediction of the effects of the at least one treatment plan and the symptoms of the condition over the first patient model, the first patient model and the second patient model representative of a digital twin of the patient that can simulate real effects on the patient in a virtual space.

15. The non-transitory computer readable storage medium of claim 14, wherein the instructions, when executed, cause the processor to present, via a user interface, the success rates, the first patient model, and the second patient model.

16. The non-transitory computer readable storage medium of claim 14, wherein the historical patient information includes historical health information, historical symptoms, and historical diagnoses.

17. The non-transitory computer readable storage medium of claim 14, wherein the instructions, when executed, cause the processor to:
associate a clinician with historical health information; and
determine clinician success rates for the at least one treatment plan.

18. The non-transitory computer readable storage medium of claim 14, wherein the instructions, when executed, cause the processor to transfer the health information to the past patient database when treatment is complete as determined by a clinician administering the treatment.

19. The apparatus of claim 1, wherein the first patient model is a first deep learning neural network, the second patient model is a second deep learning neural network, the health tracking information includes at least one of time spent resting, time spent active, daily weight gain, daily weight loss, or resting heart rate associated with the patient, and the model generator to update at least one of the first deep learning neural network or the second deep learning neural network with at least one of the time spent resting, the time spent active, the daily weight gain, the daily weight loss, or the resting heart rate.

20. The method of claim 8, wherein the first patient model is a first deep learning neural network, the second patient model is a second deep learning neural network, the health tracking information includes at least one of time spent resting, time spent active, daily weight gain, daily weight loss, or resting heart rate associated with the patient, and the model generator to update at least one of the first deep learning neural network or the second deep learning neural network with at least one of the time spent resting, the time spent active, the daily weight gain, the daily weight loss, or the resting heart rate.

21. The non-transitory computer readable storage medium of claim 14, wherein the first patient model is a first deep learning neural network, the second patient model is a second deep learning neural network, the health tracking information includes at least one of time spent resting, time spent active, daily weight gain, daily weight loss, or resting heart rate associated with the patient, and the instructions, when executed, cause the processor to update at least one of the first deep learning neural network or the second deep learning neural network with at least one of the time spent resting, the time spent active, the daily weight gain, the daily weight loss, or the resting heart rate.

* * * * *